(12) United States Patent
Barlocco et al.

(10) Patent No.: US 7,115,633 B2
(45) Date of Patent: Oct. 3, 2006

(54) BENZOSUBERONYLPIPERDINE COMPOUNDS AS ANALGESICS

(75) Inventors: Daniela Barlocco, Milan (IT); Giorgio Cignarella, Milan (IT); Giuseppe Giardina, Milan (IT); Mario Grugni, Milan (IT); Silvano Ronzoni, Milan (IT)

(73) Assignee: GlaxoSmithKline S.p.A., Verona (IT)

( * ) Notice: Subject to any disclaimer, the term of this patent is extended or adjusted under 35 U.S.C. 154(b) by 408 days.

(21) Appl. No.: 10/275,242

(22) PCT Filed: May 1, 2001

(86) PCT No.: PCT/EP01/04943

§ 371 (c)(1),
(2), (4) Date: Jul. 30, 2003

(87) PCT Pub. No.: WO01/83454

PCT Pub. Date: Nov. 8, 2001

(65) Prior Publication Data

US 2004/0029917 A1 Feb. 12, 2004

(30) Foreign Application Priority Data

May 4, 2000 (GB) .................................. 0010819.1

(51) Int. Cl.
*A61K 31/445* (2006.01)
*C07D 211/14* (2006.01)
(52) U.S. Cl. ........................ 514/319; 546/206; 546/205
(58) Field of Classification Search ................ 514/319; 546/205, 206

See application file for complete search history.

(56) References Cited

U.S. PATENT DOCUMENTS 3,462,436 A 8/1969 Fouche
3,476,761 A 11/1969 Fouche

FOREIGN PATENT DOCUMENTS

WO   WO 00 27815   5/2000

*Primary Examiner*—Kamal A. Saeed
(74) *Attorney, Agent, or Firm*—Andrea L. Winslow; Theodore R. Furman; Charles M. Kinzig

(57) ABSTRACT

Compounds of formula (I) or a derivative thereof, wherein; R is $C_{1-6}$alkyl, $C_{3-7}$cycloalkyl, $C_{1-6}$alkoxy, hydroxy, halo, $C_{1-6}$alkenyl, $C_{1-6}$alkynyl, amino, $C_{1-6}$alkylamino, di($C_{1-6}$alkyl)amino, hydroxy$C_{1-6}$alkyl, $C_{1-6}$alkoxy$C_{1-6}$alkyl, amino$C_{1-6}$alkyl, ($C_{1-6}$alkyl)amino$C_{1-6}$alkyl, di($C_{1-6}$alkyl)amino$C_{1-6}$alkyl; $R^1$ is hydrogen or R; $R^2$ is hydroxy, $C_{1-6}$alkoxy, amino, $C_{1-6}$alkylamino, di($C_{1-6}$alkyl)amino; $R^3$ is hydrogen or $C_{1-6}$alkyl; $R^4$ and $R^5$ are each independently selected from the list consisting of perhalo$C_{1-6}$alkyl, hydrogen, halo, $C_{1-6}$alkyl, $C_{1-6}$alkoxy, hydroxy, amino, $C_{1-6}$alkylamino, di($C_{1-6}$alkyl)amino, hydroxy$C_{1-6}$alkyl, $C_{1-6}$alkoxy$C_{1-6}$alkyl, amino$C_{1-6}$alkyl, ($C_{1-6}$alkyl)amino$C_{1-6}$alkyl, di($C_{1-6}$alkyl) amino$C_{1-6}$alkyl, aryl, and COX wherein X may be hydroxy, $C_{1-6}$alkoxy, $C_{1-6}$alkyl, amino, $C_{1-6}$alkylamino, or di($C_{1-6}$alkyl)amino; with the proviso that, when $R^3$ is hydrogen, then $R^4$ and $R^5$ are not both hydrogen; and wherein any alkyl group or the alkyl moiety of any group containing such a moiety may be substituted one or more times by halo; are ligands of the ORL-1 receptor and are useful in therapy.

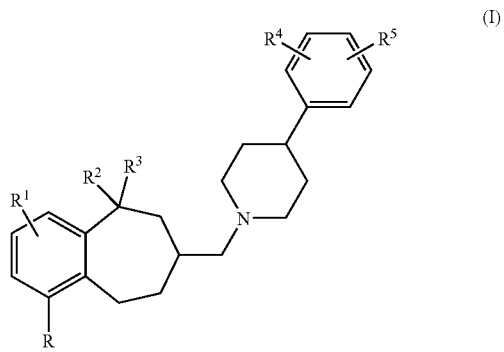

(I)

29 Claims, No Drawings

BENZOSUBERONYLPIPERDINE COMPOUNDS AS ANALGESICS

The present invention relates to certain novel compounds, to processes for preparing such compounds, to pharmaceutical compositions containing such compounds, and to the use of such compounds in medicine.

The ORL-1 receptor is found throughout the whole of the neuraxis and is known to be involved in the transmission of pain.

Eur. J. Med. Chem. 1978; 13:533–547 (Eirin et al.) discloses (±)-3-[(4-phenylpiperidin-1-yl)methyl]-1-oxo-2H-3,4-diydronaphthalene for use as a neuroleptic agent An. Real. Acad. Farm. 1989;55:461–469 (Santana et al.) discloses (±)-2-[(4-phenylpiperidin-1-yl)methyl]-1,2,3,4-tetrahydronaphthalene as an antidopaminergic agent. U.S. Pat. No. 4,022,791 (Pfizer Inc.) discloses certain 2-aminomethyl-3,4-dihydronaphthalenes as analgesics. J. Med. Chem. 1977; 20(5):699–705 (Welch et al) discloses 5,8-disubstituted 1-tetralones as analgesics and tranquillisers. J. Med. Chem. 1978;21(3):257–263 (Welch et al) discloses certain 5,8-disubstituted 2-aminomethyl-3,4-dihydronaphthalenes as analgesics and tranquillisers. International Application Publication Number WO 98/36749 (Bristol-Myers Squibb) discloses certain tetralone derivatives as antiarrhythmic agents. United Kingdom Patent Application GB 2177085 (Imperial Chemical Industries PLC) discloses certain benzocycloalkylmethylamines as fungicides. WO 99/06397 (Abbott Laboratories) discloses certain piperidine compounds useful as endothelin antagonists. WO 98/02432 (Takeda Chemical Industries Ltd) discloses certain phenylpiperidino compounds useful for the treatment of lower urinary tract infections. WO 96/22977 (Suntory Limited) discloses certain piperidinyl derivatives for treating symptoms of ischaemic diseases and preventing cytotoxic calcium overload. WO 97/23458 (Cocensys Inc.) discloses certain tetrahydronaphthyl and piperidine derivatives as sub-type selective N-methyl-D-aspartame receptor ligands. U.S. Pat. No. 5,436,255 Pfizer Inc.) discloses certain 3-piperidino-1-chromanof derivatives for blocking the NMDA receptor site. WO 95/00131 (University of Virginia Commonwealth) discloses certain amine derivatives as useful in the treatment of CNS disorders. European Patent Application EP 0 745 598 (Adir et Compagnie) discloses certain piperazine, piperidine, and tetrahydropyridine compounds as ligands of the $D_4$ dopamine receptor. EP 0 742 207 (Eisai Co. Ltd.) discloses certain cyclic amines as having acetyleholine esterase activity. U.S. Pat. No. 5,215,989 (Merck & Co. Inc.) discloses certain disubstituted piperazine and imidazole derivatives useful as Class III antiarrhythmic agents. WO 93/00313 (University of Virginia Commonwealth) discloses certain amine derivatives as selective sigma receptor binding agents. EP 0 479 601 (Ajinomoto K K) discloses certain piperidine derivatives as antiarrhythmic agents. Japanese Patent Application JP 2169 569 (Eisai K K) discloses certain cyclic amine derivatives for the treatment or prophylaxis of e.g. senile dementia, cerebral apoplexy, and cerebral atherosclerosis. WO 00/06545 (Schering Corporation) discloses certain piperidine and tetrahydropyridine derivatives as ORL-1 receptor ligands. WO 00/14067 (F. Hofmann-La Roche AG) discloses certain piperidine derivatives as ligands for the OFQ (ORL-1) receptor. WO 98/51687 (Fujisawa Pharmaceutical Co.) discloses certain piperidino derivatives as promoters of growth hormone release. WO 98/33758 (Takeda Chemical Industries) discloses certain bicyclic quinone compounds. GB 2292558 (Merck and Co.) discloses certain bicyclic compounds as fibrinogen receptor antagonists. WO 00/55137 (Axys Pharmaceuticals) discloses certain bicyclic compounds as modulators of estrogen receptors. WO 00/32582 (Glaxo Group Limited) discloses benzamide derivatives as APOB-100 secretion inhibitors. WO 00/27815 (SmithKline Beecham SpA) discloses N-substituted azacycles as ORL-1 inhibitors. WO 00/12074 (Scios Inc.) discloses certain piperidines and piperazines as inhibitors of P-38 alpha kinase. WO 98/38156 (Takeda Chemical Industries Ltd.) discloses certain amino compounds and their use as amyloid-beta production inhibitors. EP 846683 (F. Hoffmann La Roche AG) discloses certain hydroxypiperidine derivatives.

It has now surprisingly been found that certain benzosuberonylpiperidine derivatives are ligands of the ORL-1 receptor, and therefore may be useful as analgesics in humans or animals for the treatment of, for example, acute pain; chronic neuropathic or inflammatory pain including post herpetic neuralgia; neuralgia; diabetic neuropathy and post stroke pain; osteoarthritis/back pain; painful pregnancy labour; and therapy of opioid tolerance and dependence.

These compounds may also therefore be useful in the treatment or prophylaxis of eating disorders such as anorexia and bulimia; anxiety and stress conditions; immune system diseases; cardiovascular system dysfunctions; memory loss; cognitive disorders; motor impairment and neurodegeneration owing to Alzheimer's disease; senile dementia; Parkinson's disease or other neurodegenerative pathologies; stroke; epilepsy; altered diuresis and sodium excretion; syndrome of inappropriate secretion of antidiuretic dormone (SIADH); adult respiratory distress syndrome (ARDS); congestive heart failure; cirrhosis with ascites; sexual dysfunctions including impotence and frigidity; and altered pulmonary function, including chronic obstructive pulmonary disease.

These compounds may also therefore be useful in the treatment or prophylaxis of cough; asthma; depression; drug abuse such as alcohol abuse; dementias such as vascular dementia and AIDS dementia complex; metabolic disorders such as obesity; arterial blood pressure disorders; and for the control of water balance and sodium excretion.

Accordingly, the present invention provides a compound of formula (I)

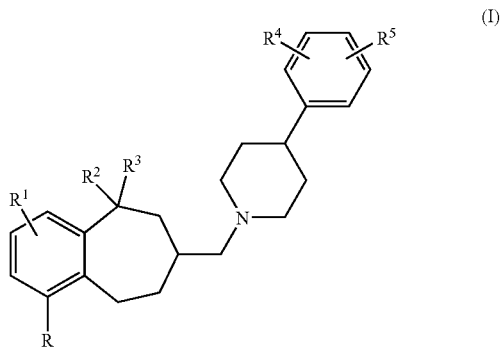

or a derivative thereof, wherein;

R is $C_{1-6}$alkyl, $C_{3-7}$cycloalkyl, $C_{1-6}$alkoxy, hydroxy, halo, $C_{1-6}$alkenyl, $C_{1-6}$alkynyl, amino, $C_{1-6}$alklylamino, di($C_{1-6}$alkyl)amino, hydroxy$C_{1-6}$alkyl, $C_{1}$-6alkoxy$C_{1-6}$alkyl, amino$C_{1-6}$alkyl, ($C_{1-6}$alkyl)amino$C_{1-6}$alkyl, di($C_{1-6}$alkyl)amino$C_{1-6}$alkyl;

$R^1$ is hydrogen or R;

$R^2$ is hydroxy, $C_{1-6}$alkoxy, amino, $C_{1-6}$alkylamino, di($C_{1-6}$ allyl)amino;

$R^3$ is hydrogen or $C_{1-6}$alkyl;

$R^4$ and $R^5$ are each independently selected from the list consisting of perhalo$C_{1-6}$alkyl, hydrogen, halo, $C_{1-6}$alkyl, $C_{1-6}$alkoxy, hydroxy, amino, $C_{1-6}$alkylamino, di($C_{1-6}$alkyl)amino, hydroxy$C_{1-6}$alkyl, $C_{1-6}$alkoxy$C_{1-6}$alkyl, amino$C_{1-6}$alkyl, ($C_{1-6}$alkyl)amino$C_{1-6}$alkyl, di($C_{1-6}$alkyl)amino$C_{1-6}$alkyl, aryl, and COX wherein X may be hydroxy, $C_{1-6}$alkoxy, $C_{1-6}$alkyl, amino, $C_{1-6}$alkylamino, or di($C_{1-6}$alkyl)amino; with the proviso that, when $R^3$ is hydrogen, then $R^4$ and $R^5$ are not both hydrogen; and wherein any alkyl group or the alkyl moiety of any group containing such a moiety may be substituted one or more times by halo.

Suitably, R is $C_{1-6}$alkenyl, $C_{1-6}$alkyl, halo, or $C_{1-6}$alkoxy.

Favourably, R is vinyl, allyl, ethyl, methyl, fluoro, bromo, or methoxy.

Preferably, R is methyl, fluoro, or bromo.

More preferably, R is methyl.

Suitably, $R^1$ is hydrogen or methyl.

Favourably, $R^1$ is hydrogen or 4-methyl.

Suitably, $R^2$ is hydroxy.

Favourably, $R^3$ is hydrogen or methyl.

Preferably, $R^3$ is hydrogen.

Suitably, $R^4$ is hydroxy$C_{1-6}$alkyl, halo, perhalo$C_{1-6}$alkyl, $C_{1-6}$alkyl, or hydrogen.

Favourably, $R^4$ is hydroxymethyl, fluoro, trifluoromethyl, chloro, methyl, bromo, or hydrogen.

More favourably, $R^4$ is 2-hydroxymethyl, 2-F, 2-$CF_3$, 2-Cl, 2-Me, 3-Me, 2-Br, or hydrogen.

Preferably, $R^4$ is 2-Cl, 2-F, 2-Me, or 2-Br.

More preferably, $R^4$ is 2-Cl or 2-Me.

Suitably, $R^5$ is $C_{1-6}$alkyl, hydrogen, or halo.

Favourably, $R^5$ is methyl, hydrogen, fluoro, or chloro.

More favourably, $R^5$ is hydrogen, 6-Me, 3-F, 5-F, 6-F, or 6-Cl.

Preferably, $R^5$ is hydrogen, 3-F, 6-Me, 6-F, or 6-Cl.

More preferably, $R^5$ is 6-Me, 6-F, or 6-Cl.

Preferred compounds of formula (I) are Examples 1, 3, 4, 6, 8, 11, 14, 15, 19, 21, 24, 26, 22, 25, 16, and 18.

Compounds of formula (I) which are more preferred are Examples 26, 22, 25, 16, and 18.

Suitable derivatives of the compounds of the invention are pharmaceutically acceptable derivatives.

Suitable derivatives of the compounds of the invention include salts and solvates.

Suitable pharmaceutically acceptable derivatives include pharmaceutically acceptable salts and pharmaceutically acceptable solvates.

Suitable pharmaceutically acceptable salts include metal salts, such as for example aluminium, alkali metal salts such as lithium, sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)amine or tri-(2-hydroxyethyl)amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine, quinine or quinoline.

Suitable pharmaceutically acceptable salts also includes pharmaceutically acceptable acid addition salts, such as those provided by pharmaceutically acceptable inorganic acids or organic acids.

Suitable pharmaceutically acceptable acid addition salts provided by pharmaceutically acceptable inorganic acids includes the sulphate, nitrate, phosphate, borate, hydrochloride hydrobromide and hydroiodide.

Suitable pharmaceutically acceptable acid addition salts provided by pharmaceutically acceptable organic acids includes the acetate, tartrate, maleate, fumarate, malonate, citrate, succinate, lactate, oxalate, benzoate, ascorbate, methanesulphonate, α-ketoglutarate and α-glycerophosphate, acetate, fumarate, salicylate, mandelate, and methanesulphonate.

Suitable pharmaceutically acceptable solvates include hydrates.

The compounds of formula (I) or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula (I) or its salt or solvate.

One preferred pharmaceutically acceptable form is the crystalline form, including such form in a pharmaceutical composition. In the case of salts and solvates the additional ionic and solvent moieties must also be non-toxic.

Unless otherwise stated, "alkyl" groups referred to herein, including those forming part of other groups, include straight or branched chain alkyl groups containing up to twelve, suitably up to six carbon atoms. These alkyl groups may be optionally substituted with up to five, suitably up to three, groups selected from the list consisting of alkoxy, amino, carboxy and esters thereof, cyano, hydroxy, and halogen.

Unless otherwise stated, "alkenyl" and "alkynyl" groups referred to herein include straight and branched chain groups containing from two to twelve, suitably from two to six, carbon atoms. These alkenyl and alkynyl groups may be optionally substituted with up to five, suitably up to three, groups including those substituents described hereinbefore for the alkyl groups.

Unless otherwise stated, "cycloalkyl" groups referred to herein include groups having between three and eight ring carbon atoms. These cycloalkyl groups may be optionally substituted with up to five, suitably up to three, groups including those substituents hereinbefore described for the alkyl groups.

Unless otherwise stated, "aryl" includes phenyl, naphthyl, and biphenyl groups, especially phenyl.

Suitable optional substituents for any aryl group include up to five, suitably up to three, groups selected from the list consisting of alkylnyl, amino, hydroxyalkyl, aminoalkyl, mono-and di-alkylaminoalkyl, alkyl, alkylsulphonylamino, mono- and di-alkylamino, mono- and di-alkylaminocarbonyl, arylcarbonyl, aralkoxy, arylcarbonylamino, aminocarbonyl, aryl, alkylaminocarbonyl, halo, alkyl, alkenyl, aralkyl, alkoxy, alkoxyalkyl, hydroxy, nitro, amino, cyano, mono- and di-alkylamino, acyl, acylamino, acyloxy, carboxy and esters thereof, carbamoyl, aryloxy, cycloalkyl, and heterocyclyl.

Unless otherwise stated, "heterocyclyl" and "heterocyclic" suitably include aromatic and non-aromatic, single and fused, rings suitably containing up to four heteroatoms in each ring, each of which is selected from oxygen, nitrogen and sulphur. Each ring suitably has from 4 to 7, preferably 5 or 6, ring atoms. These heterocyclyl and heterocyclic rings may be unsubstituted or substituted by up to five substituents. A fused heterocyclic ring system may include carbocyclic rings and need include only one heterocyclic ring. Examples include pyridyl, indolinyl, quinolinyl, indolyl, benzoxazolyl, benzothiazolyl, benzothiazolinonyl, and benzoxazolinonyl.

Substituents for any heterocyclyl or heterocyclic group are suitably selected from cyano, alkyl, aminocarbonyl, nitro, aryl, arylcarbonyl, aryloxy, alkylcarbonyl, halogen, alkyl, aralkyl, alkoxy, hydroxy, amino, carboxy and salts and esters thereof, and aryl.

Unless otherwise stated, the terms "halogen" or "halo" include iodo, bromo, chloro and fluoro; especially chloro, fluoro, and bromo.

Certain of the compounds of formula (I) may contain chiral atoms and/or multiple bonds, and hence may exist in one or more stereoisomeric forms. The present invention encompasses all of the isomeric forms of the compounds of formula (I) whether as individual isomers or as mixtures of isomers, including geometric isomers, tautomers, enantiomers, and racemic modifications.

It has been found that, where a compound of formula (I) exhibits optical isomerism, one enantiomer possesses a greater affinity for the ORL-1 receptor than its antipode.

Accordingly, the present invention also provides an enantiomer of a compound of formula (I) or a derivative thereof.

In a further aspect, the present invention provides a mixture of enantiomers of a compound of formula (I), or a derivative thereof, wherein one enantiomer is present in a greater proportion than its antipode.

A further aspect of the invention provides a process for the preparation of a compound of formula (I) wherein $R^2$ is hydroxy and $R^3$ is hydrogen, and thereafter, if required, carrying out one or more of the following optional steps:

(i) converting a compound of formula (I) to another compound of formula (I);
(ii) removing any necessary protecting group;
(iii) preparing an appropriate derivative of the compound so formed; which process comprises either;

Process A. the reduction of a compound of formula (II)

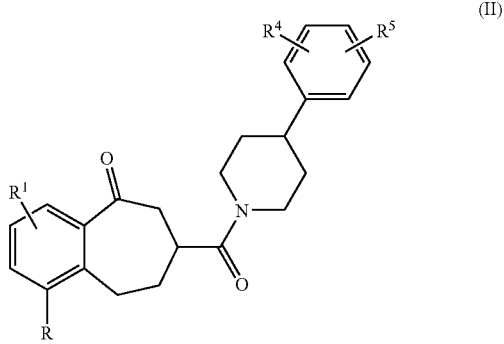

wherein;

R, $R^1$, $R^4$, and $R^5$ are as hereinbefore defined for formula (I) with a suitable reducing agent such as a metal hydride or a borane-containing reducing agent, or;

Process B. reacting a compound of formula (III)

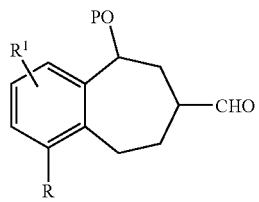

wherein;

R and $R^1$ are as hereinbefore defined for formula (I) and P represents a protecting group such as a silyl group, with a compound of formula (I)

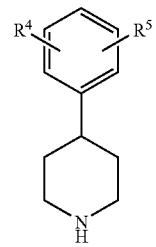

wherein;

$R^4$ and $R^5$ are as hereinbefore defined for formula (I), under reductive amination conditions such as sodium cyanoborohydride in methanol or acetonitrile (Lane, *Synthesis*, 135, 1975) and thereafter removing the protecting group using for example mild acid hydrolysis or a fluorinated reagent such as tetra-N-butylammonium fluoride to yield the compound of formula (I) wherein $R^2$ is hydroxy and $R^3$ is hydrogen. A suitable protecting group is a silyl group. Procedures for the protection and deprotection of substituent groups are discussed in Greene and Wuts *Protective Groups in Organic Synthesis*, III Edition, Wiley, New York, (1999).

For a compound of formula (I) wherein $R^2$ is hydroxy and $R^3$ is hydrogen, Process A is the preferred process.

For Process A in general, a solution of a compound of formula (II) and a suitable reducing agent in a suitable dry solvent is prepared under a suitable inert atmosphere at a suitable initial temperature and is then stirred at a suitable reaction temperature for a suitable period of time. A suitable reducing agent is lithium aluminium hydride, lithium aluminium hydride/aluminium trichloride, or diisobutylaluminium hydride. A suitable solvent is tetrahydrofuran or diethyl ether. A suitable inert atmosphere is an atmosphere of nitrogen. A suitable initial temperature is in the range 0–4° C. A suitable reaction temperature is in the range 15° C. to the reflux temperature of the solvent. A suitable period of time is 2–18 hours. The mixture is then quenched, basified, filtered if necessary, then, if necessary, extracted into a suitable organic solvent. The solvent is then removed and the crude product purified. Suitable quenching media are water and saturated aqueous sodium potassium tartrate tetrahydrate solution. A suitable base is aqueous sodium hydroxide solution. A suitable organic extraction solvent is diethyl ether. Conventional methods of cooling and heating such as ice/salt baths and electric heating mantles may be employed. Conventional methods of purification such as flash chromatography, trituration, and crystallisation may be employed.

In a preferred aspect of Process A, a solution of aluminium trichloride in dry diethyl ether is added dropwise at 0° C. to a suspension of lithium aluminium hydride in dry diethyl ether under an atmosphere of nitrogen After stirring for ten minutes, a solution of the compound of formula (II) in dry diethyl ether is added dropwise, the reaction mixture allowed to warm to ambient temperature, and stirred for four hours. After cooling to 0° C., the reaction is quenched by the sequential addition of water, 15% aqueous sodium hydroxide solution, and water. The aqueous phase is extracted with diethyl ether, the organic phase is collected, dried with, for example, magnesium sulphate and the solvent is removed by evaporation. The crude product is purified by flash chromatography followed by trituration.

A compound of formula (II) may be prepared by reaction of a suitably activated compound of formula (V)

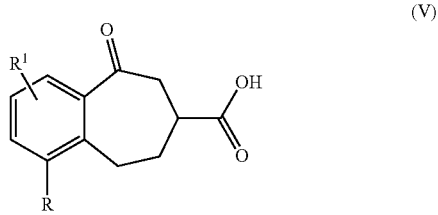

(V)

wherein;

R and $R^1$ as hereinbefore defined for formula (I), with a compound of formula (IV) as hereinbefore defined.

Compounds of formula (V) may suitably be activated prior to reaction with the compound of formula (V) by formation of the corresponding acyl halide, for example by reaction of the compound of formula (II) with a halodehydroxylation agent such as oxalyl chloride. Compounds of formula (V) may also be activated in situ i.e. in the presence of the compound of formula (IV) by the use of activating agents such as dicyclohexylcarbodiimide/1-hydroxybenzotriazole, N-ethyl-N'-(3-dimethylaminopropyl)carbodiimide/1-hydroxybenzotriazole, or O-benzotriazol-1-yl-N,N,N',N'-tetramethyluronium hexafluorophosphate.

In general, a compound of formula (II) may be prepared as follows: To a solution of a compound of formula (V) in a suitable dry solvent at a suitable initial temperature under a suitable inert atmosphere is added a suitable halodehydroxylation agent The solution is warmed to a suitable reaction temperature and for a suitable period of time and the solvent removed under reduced pressure. A suitable solvent is dichloromethane. A suitable initial temperature is in the range of −2° C. to 4° C. A suitable inert atmosphere is a nitrogen atmosphere. A suitable halodehydroxylation agent is oxalyl chloride. A suitable reaction temperature is in the range of 15° C. to 25° C. A suitable period of time is 12 to 18 hours. Conventional methods of cooling and heating such as ice/salt baths and electric heating mantles may be employed. The crude acid halide is then reacted with the compound of formula (IV) without further purification in the following manner: At a suitable initial temperature and under a suitable inert atmosphere, a solution of the crude acid halide in a suitable dry solvent is added to a solution of the compound of formula (IV), or a salt thereof, and a suitable hindered base in a suitable dry solvent. A suitable initial temperature is in the range of −2° C. to 4° C. A suitable inert atmosphere is an atmosphere of nitrogen. A suitable solvent for the acid halide, and the compound of formula (IV) and the hindered base is dichloromethane. A hindered base is a base which does not act as a competing nucleophile, such as triethylamine. The reaction mixture is allowed to warm to a suitable reaction temperature for a suitable period of time, water added, and the organic phase separated, washed with a dilute aqueous solution of a suitable mineral acid and dried with, for example, magnesium sulphate. A suitable reaction temperature is in the range of 15° C. to 25° C. A suitable period of time is 12 to 18 hours. A suitable mineral acid is hydrochloric acid. The crude compound of formula (II) may be purified by conventional methods of purification such as flash chromatography, crystalisation, and trituration. Conventional methods of cooling and heating such as ice/salt baths and electric heating mantles may be employed.

In a preferred aspect, the compound of formula (V) is dissolved in dry dichloromethane and oxalyl chloride added dropwise at 0° C. under an atmosphere of nitrogen. The solution is allowed to warm to ambient temperature for about 15 hours and the solvent and excess oxalyl chloride removed under reduced pressure. The resulting acid chloride is dissolved in dry dichloromethane, added to a solution of the hydrochloride of the compound of formula (IV) and triethylamine in dichloromethane at 0° C. and allowed to warm to ambient temperature for about 15 hours. Water is then added, the organic phase separated, washed with 1M aqueous hydrochloric acid and dried with, for example, magnesium sulphate. The solvent is removed under reduced pressure and the crude compound of formula (II) purified by flash chromatography.

Compounds of formula (V) may be prepared as described in Bowman, *Tetrahedron,* 48, 4027, (1992), or Hasegawa, *Tetrahedron Lett.,* 39, 4059, (1998), or may be prepared by transforming the hydroxy group of an alcohol of formula (XII) into a suitable leaving group such as methanesulphonate, p-toluenesulphonate or bromide, and reacting said compound with diethyl malonate in presence of a base such as sodium ethoxide to obtain a compound of formula (XOI). The compound of formula (XI) is then alkylated with t-butyl bromoacetate in the presence of a base such as sodium hydride to yield a compound of formula (XIV). The t-butyl ester is then selectively hydrolysed with, for example trifluoroacetic acid to yield the carboxylic acid (XV), which is thereafter converted to the corresponding acyl chloride, cyclised under Friedel-Crafts conditions and subsequently hydrolysed and decarboxylated using conventional methods. See Scheme 1.

Scheme 1

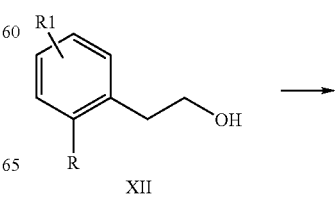

XII

-continued

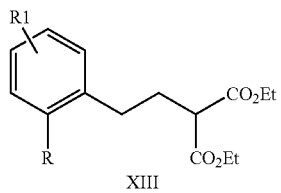
XIII

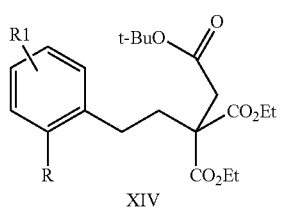
XIV

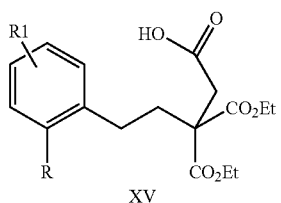
XV

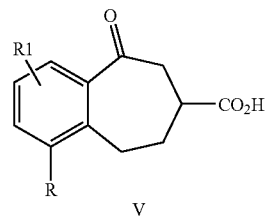
V wherein R and $R^1$ are as hereinbefore defined for formula (I).

Compounds of formula (IV) may be prepared as described in Elliott, *Bioorg. Med. Chem. Lett.*, 8, 1851, (1998) or may be prepared by reacting an aromatic aldehyde of formula (XVI) with ethyl acetoacetate in presence of a catalytic amount of an organic base such as piperidine, to give compound (XVII), which is thereafter hydrolysed in basic conditions for example in the presence of aqueous sodium hydroxide solution, to yield the carboxylic acid (XVIII), which is then transformed into the imide (XIX) by conversion to its ammonium salt and subsequent pyrolysis, and finally reducing said imide using a suitable metal hydride or a borane-based reagent. See Scheme 2.

Scheme 2

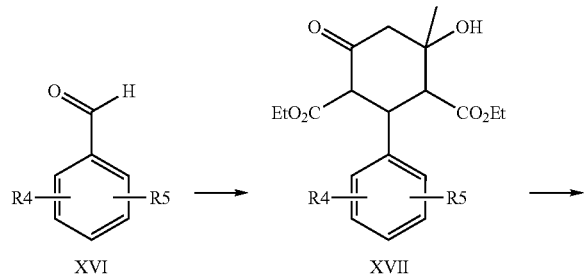
XVI → XVII →

-continued

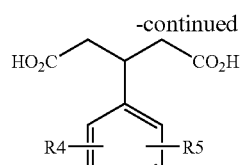
XVIII

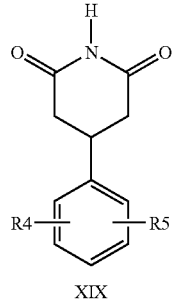 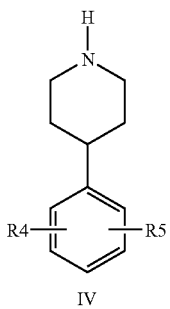
XIX              IV wherein $R^4$ and $R^5$ are as hereinbefore defined for formula (I), or by reacting a carboxylic compound of formula I, wherein P is a suitable protecting group such as benzyl, with an organometallic compound of formula (KU), wherein M represents a metal such as Li or Mg, for example aryllithium derivatives or Grignard reagents, obtaining an alcohol of formula (XII), dehydrating said alcohol to a compound of formula (XXII) in acidic conditions (e.g. conc. HCl or AcOH/$H_2SO_4$) and finally reducing and deprotecting the compound of formula (XII) via hydrogenation over a suitable catalyst (e.g. Pd on carbon or $PtO_2$) or via dissolving metal reduction (e.g. Li or Na in liquid ammonia). See Scheme 3.

Scheme 3

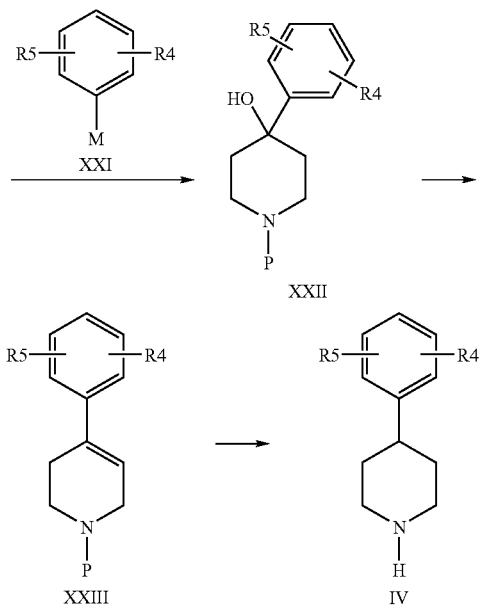

wherein $R^4$ and $R^5$ are as hereinbefore defined for formula (I).

Compounds of formula (W are known, commercially available compounds or may be prepared according to procedures described in standard reference texts of synthetic methodology such as *J. March, Advanced Organic Chemistry*, 3rd Edition (1985), *Wiley Interscience*.

Compounds of formula (XVI) are known, commercially available compounds, or may be prepared according to procedures described in standard reference texts of synthetic methodology such as *J. March, Advanced Organic Chemistry*, 3rd Edition (1985), *Wiley Interscience*.

Compounds of formula (XX) are known, commercially available compounds, or may be prepared according to procedures described in standard reference texts of synthetic methodology such as *J. March, Advanced Organic Chemistry*, 3rd Edition (1985), *Wiley Interscience*.

Compounds of formula (X) are known and may be prepared according to procedures described in standard reference texts of synthetic methodology such as *J. March, Advanced Organic Chemistry*, 3rd Edition (1985), *Wiley Interscience*.

Compounds of formula (III) may be prepared from compounds of formula (VI)

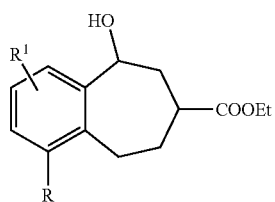

(VI)

wherein;

R and $R^1$ are as hereinbefore defined for formula (I) by protection of the hydroxy group with a suitable protecting group such as a silyl group, followed by reduction of the ester moiety to an aldehyde group using a suitable reducing agent such as diisobutylaluminium hydride (Winterfeldt, *Synthesis*, 617, (1975)).

Compounds of formula (VI) may be prepared from compounds of formula (VII)

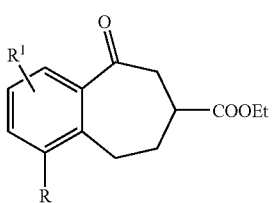

(VII)

wherein;

R and $R^1$ are as hereinbefore defined for formula (I) by conventional reduction procedures for example-using a suitable reducing agent such as sodium borohydride.

Compounds of formula (VII) may be prepared from compounds of formula (V) by conventional esterification procedures for example those described in standard reference texts of synthetic methodology such as *J. March, Advanced Organic Chemistry*, 3rd Edition (1985), *Wiley Interscience*.

In a further aspect, there is provided a process for the preparation of a compound of formula (I) wherein $R^2$ is hydroxy and $R^3$ is $C_{1-6}$alkyl, which process comprises the oxidation of a compound of formula (a) wherein $R^2$ is hydroxy and $R^3$ is hydrogen using a suitable oxidising agent such as $MnO_2$, PDC, or DMSO/oxalyl chloride (Swem *J. Org. Chem.* 43 2480 (1978)) to give a compound of formula (I')

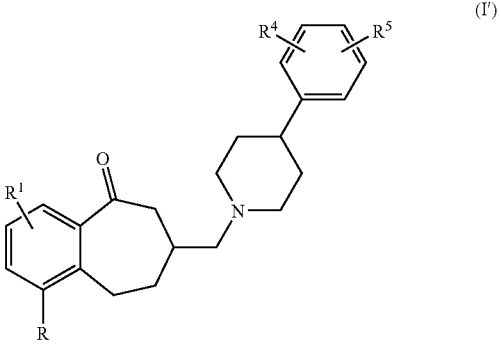

(I')

wherein;

R, $R^1$, $R^4$, and $R^5$ are as hereinbefore defined for formula (I), followed by reaction of the compound of formula (I') with a suitable organometallic compound such as an alkylmetal compound for example an alkyllithium compound, or a Grignard reagent such as an alkyl Grignard reagent, and thereafter, if required, carrying out one or more of the following optional steps:

(i) converting a compound of formula (I) to another compound of formula (I);
(ii) removing any necessary protecting group;
(iii) preparing an appropriate derivative of the compound so formed.

In general, a solution of the compound of formula (I') in a suitable dry solvent at a suitable initial temperature under a suitable inert atmosphere is added to a solution of the organometallic reagent in a suitable dry solvent. The reaction mixture is stirred at the initial temperature for a suitable initial time period, then warmed to a suitable second temperature and stirred for a suitable second time period. The mixture is then cooled to the initial temperature and quenched with a suitable quenching medium A suitable solvent for the compound of formula (I') and the organometallic reagent is diethyl ether. A suitable initial temperature is in the range −2° C. to 4° C. A suitable inert atmosphere is an atmosphere of nitrogen. A suitable initial time period is 30 minutes to 2 hours. A suitable second temperature is 15° C. to 25° C. A suitable second time period is 30 minutes to 2 hours. A suitable quenching medium is saturated aqueous ammonium chloride solution. The aqueous phase is extracted with a suitable organic solvent such as diethyl ether, the organic extract isolated, dried with for example magnesium sulphate, and the solvent removed under reduced pressure. The crude product is then purified. Conventional means of heating and cooling for example ice/salt baths and electric-heating mantles may be employed. Conventional methods of purification such as flash chromatography, crystallisation, and trituration may be employed.

In a preferred aspect, a solution of the compound of formula (I') in dry diethyl ether is added at 0° C. and under an atmosphere of nitrogen to a solution of $C_{1-6}$alkyl magnesium iodide in dry diethyl ether. The mixture is stirred at 0° C. for one hour, allowed to warm to ambient temperature and stirred for a further one hour. The mixture is then cooled to 0° C. and quenched with saturate aqueous ammonium chloride solution. The aqueous phase was extracted with diethyl ether, the organic layer separated, dried, and the solvent removed under reduced pressure. The crude compound of formula (I) wherein $R^2$ is hydroxy and $R^3$ is $C_{1-6}$alkyl is then purified by flash chromatography.

In an additional aspect, there is provided a process for the preparation of a compound of formula (I) wherein $R^2$ is amino, $C_{1-6}$alkylamino, or di($C_{1-6}$alkyl)amino and $R^3$ is hydrogen, which process comprises the reduction of a compound of formula (VIII)

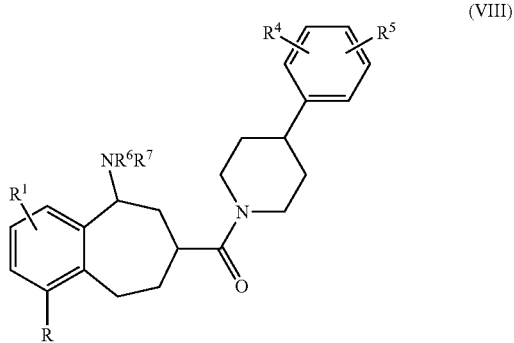

(VIII)

wherein;

R, $R^1$, $R^4$, and $R^5$ are as hereinbefore defined for formula (I) and $R^6$ and $R^7$ are each independently hydrogen or $C_{1-6}$alkyl, using a suitable reducing agent such as a metal hydride or a borane-based reagent as hereinbefore described in Process A, and thereafter, if required, carrying out one or more of the following optional steps:

(i) converting a compound of formula (I) to another compound of formula (I);
(ii) removing any necessary protecting group;
(iii) preparing an appropriate derivative of the compound so formed.

Compounds of formula (VII) may be prepared from compounds of formula (II) as hereinbefore defined by reaction with a compound of formula (IX)

$$HNR^6R^7 \quad (IX)$$

wherein;

$R^6$ and $R^7$ are each independently hydrogen or $C_{1-6}$alkyl, under reductive amination conditions as hereinbefore described in Process B.

Compounds of formula (IX) are known, commercially available compounds or may be prepared according to procedures described in standard reference texts of synthetic methodology such as *J. March, Advanced Organic Chemistry*, 3rd Edition (1985), Wiley Interscience.

The above mentioned conversion of a compound of formula (I) into another compound of formula (I) includes any conversion which may be effected using conventional procedures, but in particular the said conversions include:
(a). converting one group $R^2$ into another group $R^2$.

The above mentioned conversion (a) may be carried out using any appropriate method under conditions determined by the particular groups chosen.

Suitable conversions of one group $R^2$ into another group $R^2$, as in conversion (a), include:

(i). converting a group $R^2$ which represents hydroxy into a group $R^2$ which represents alkoxy; such a conversion may be carried out using a conventional alkylation procedure, for example treating an appropriately protected compound of formula (I) with a strong base such as sodium hydride and alkylating the resultant alkoxide anion with a suitable alkylating agent such as an alkyl halide, and;

(ii). converting a group $R^2$ which represents hydroxy into a group $R^2$ which represents amino, alkylamino, or dialkylamino; such a conversion may be carried out using a conventional dehydroxyamination procedure, for example treating an appropriately protected compound of formula (I) wherein $R^2$ is hydroxy with an activating agent such as a methanesulphonyl halide or a p-toluenesulphonyl halide to transform the hydroxy group $R^2$ into the corresponding methanesulphonate or p-toluenesulphonate respectively and thereafter reacting the activated compound with an amine of formula (IX) as hereinbefore defined in the presence of a hindered base such as triethylamine.

As has previously been mentioned, compounds of formula (I) are ligands of the ORL-1 receptor.

Accordingly, there is provided a compound of formula (I), or a pharmaceutically acceptable derivative thereof, as an active therapeutic substance.

According to another aspect of the present invention there is provided a method of modulating the ORL-1 receptor activity in a human or animal patient in need thereof, which method comprises administering to the human or animal patient an effective amount of a compound of formula (I) or a pharmaceutically acceptable derivative thereof.

In a further aspect of the present invention there is provided the use of a compound of formula (I), or a pharmaceutically acceptable derivative thereof, for modulating the ORL-1 receptor activity in a human or animal patient.

In yet another aspect of the present invention there is provided the use of a compound of formula (I), or a pharmaceutically acceptable derivative thereof, in the manufacture of a medicament for modulating the ORL-1 receptor activity in a human or animal patient.

Said compounds of formula (I) may be agonists or antagonists of the ORL-1 receptor.

Accordingly, the present invention provides the use of a compound of formula (I), or a pharmaceutically acceptable derivative thereof, as an analgesic for the treatment of, for example, acute pain; chronic neuropathic or inflammatory pain including post herpetic neuralgia; neuralgia; diabetic neuropathy and post stroke pain; osteoarthritis/back pain; painful pregnancy labour, and therapy of opioid tolerance and dependence.

Accordingly, the present invention further provides the use of a compound of formula (I), or a pharmaceutically acceptable derivative thereof, in the treatment or prophylaxis of eating disorders such as anorexia and bulimia; anxiety and stress conditions; immune system diseases; cardiovascular system dysfunctions; memory loss; cognitive disorders; motor impairment and neurodegeneration owing to Alzheimer's disease; senile dementia; Parkinson's disease or other neurodegenerative pathologies; stroke; epilepsy; altered diuresis and sodium excretion; syndrome of inappropriate secretion of antidiuretic hormone (SLADH); adult respiratory distress syndrome (ARDS); congestive heart failure; cirrhosis with ascites; sexual dysfunctions including impotence and frigidity; and altered pulmonary function, including chronic obstructive pulmonary disease.

Accordingly, the present invention also provides the use of a compound of formula (I), or a pharmaceutically acceptable derivative thereof, in the treatment or prophylaxis of cough; asthma; depression; drug abuse such as alcohol abuse; dementias such as vascular dementia and AIDS dementia complex; metabolic disorders such as obesity; arterial blood pressure disorders; and for the control of water balance and sodium excretion.

In a further aspect, the present invention provides the use of a compound of formula (I), or a pharmaceutically acceptable derivative thereof, for the manufacture of a medicament as an analgesic for the treatment of, for example, acute pain; chronic neuropathic or inflammatory pain including post herpetic neuralgia; neuralgia; diabetic neuropathy and post stroke pain; osteoarthritis/back pain; painful pregnancy labour; and therapy of opioid tolerance and dependence.

In an additional aspect, the present invention provides the use of a compound of formula (I), or a pharmaceutically acceptable derivative thereof, for the manufacture of a medicament for the treatment or prophylaxis of eating disorders such as anorexia and bulimia; anxiety and stress conditions; immune system diseases; cardiovascular system dysfunctions; memory loss; cognitive disorders; motor impairment and neurodegeneration owing to Alzheimer's disease; senile dementia; Parkinson's disease or other neurodegenerative pathologies; stroke; epilepsy; altered diuresis and sodium excretion; syndrome of inappropriate secretion of antidiuretic hormone (SIADM); adult respiratory distress syndrome (ARDS); congestive heart failure; cirrhosis with ascites; sexual dysfunctions including impotence and frigidity; and altered pulmonary function, including chronic obstructive pulmonary disease.

In yet a further aspect, the present invention provides the use of a compound of formula (I), or a pharmaceutically acceptable derivative thereof, for the manufacture of a medicament for the treatment or prophylaxis of cough; asthma; depression; drug abuse such as alcohol abuse; dementias such as vascular dementia and AIDS dementia complex; metabolic disorders such as obesity; arterial blood pressure disorders; and for the control of water balance and sodium excretion.

Accordingly, in a further aspect, there is provided a method of treatment of acute pain; chronic neuropathic or inflammatory pain including post herpetic neuralgia; neuralgia; diabetic neuropathy and post stroke pain; osteoarthritis back pain; painful pregnancy labour, and therapy of opioid tolerance and dependence, which method comprises the administration of a compound of formula (I), or a pharmaceutically acceptable derivative thereof, to the mammal in need thereof.

In a further aspect, there is provided a method of treatment or prophylaxis of eating disorders such as anorexia and bulimia; anxiety and stress conditions; immune system diseases; cardiovascular system dysfunctions; memory loss; cognitive disorders; motor impairment and neurodegeneration owing to Alzheimer's disease; senile dementia; Parkinson's disease or other neurodegenerative pathologies; stroke; epilepsy; altered diuresis and sodium excretion; syndrome of inappropriate secretion of antidiuretic hormone (SIADH); adult respiratory distress syndrome (ARDS); congestive heart failure; cirrhosis with ascites; sexual dysfunctions including impotence and frigidity; and altered pulmonary function, including chronic obstructive pulmonary disease, which method comprises the administration of a compound of formula (I), or a pharmaceutically acceptable derivative thereof, to the mammal in need thereof.

In yet a further aspect, there is provided a method of treatment or prophylaxis of cough; asthma; depression; drug abuse such as alcohol abuse; dementias such as vascular dementia and AIDS dementia complex; metabolic disorders such as obesity; arterial blood pressure disorders; and for the control of water balance and sodium excretion, which method comprises the administration of a compound of formula (I), or a pharmaceutically acceptable derivative thereof, to the mammal in need thereof.

Administration of a compound in accordance with the invention may be by way of oral, sublingual, transdermal or parenteral administration.

An effective amount of the compound of the invention will depend on factors such, for example, as the nature and severity of the disorder(s) being treated and on the weight of the mammal. However, a unit does will normally contain 0.1 to 50 mg, for example 0.5 to 10 mg, of the compound. Unit doses will normally be administered once or more than once a day, for example 2, 3, or 4 times a day, more usually 1 to 3 times a day, such that the total daily dose is normally in the range, for a 70 kg adult of 0.1 to 50 mg, for example 0. 1 to 5 mg, that is in the range of approximately 0.001 to 1 mg/kg/day, more usually 0.005 to 0.2 mg/kg/day.

For oral or parenteral administration, it is greatly preferred that the compound is administered in the form of a unit dose composition, such as a unit dose oral or parenteral composition.

Accordingly, in yet another aspect of the present invention there is also provided a pharmaceutical composition comprising a compound of formula (I), or a pharmaceutically acceptable derivative thereof, and a pharmaceutically acceptable carrier.

Such compositions are prepared by admixture and are suitably adapted for oral or parenteral administration, and as such may be in the form of tablets, capsules, oral preparations, powders, granules, lozenges, reconstitutable powders, injectable and liquid infusible solutions or suspensions or suppositories.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers include cellulose, mannitol, lactose and other similar agents.

Suitable disintegrants include starch, polyvinylpyrrolidone and starch derivatives such as sodium starch glycolate.

Suitable lubricants include, for example, magnesium stearate.

Suitable pharmaceutically acceptable wetting agents include sodium lauryl sulphate.

These solid oral compositions may be prepared by conventional methods of blending, filling or tabletting. Repeated blending operations may be used to distribute the active agent throughout those compositions employing large quantities of fillers. Such operations are conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms may be prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also-dissolved in the vehicle. To enhance the stability, the composition may be frozen after filling into the vial and the water removed under vacuum.

Parenteral suspensions are prepared in substantially the same manner except that the compound may be suspended in the vehicle instead of being dissolved and sterilised by exposure to ethylene oxide before suspending in the sterile vehicle. Advantageously, a surfactant or wetting agent may be included in the composition to facilitate uniform distribution of the compound of the invention.

As is common practice, the compositions will usually be accompanied by written or printed directions for use in the treatment concerned.

Preparation 1

2-Methylphenethyl alcohol methanesulphonate 10 g (0.0734 mol) of 2-methylphenethyl alcohol were dissolved in 200 mL of dry $CH_2Cl_2$ under a nitrogen atmosphere; the solution was cooled to 5° C., 16.4 mL (0.1175 mol) of triethylamine were added, followed by a solution of 9.1 mL (0.1175 mol) of methanesulphonyl chloride in 100 mL of dry $CH_2Cl_2$, keeping the temperature below 15° C. The reaction mixture was allowed to warm to room temperate in 2 h, then 250 mL of water were added, the organic phase was collected and the solvent was removed in vacuo. The resulting oil was taken up in $Et_2O$, the organic phase was washed with 1N HCl and with saturated $NaHCO_3$ solution, then it was dried and the solvent was removed in vacuo, yielding 14.5 g of the title product which was used without further purification.

IR, $^1H$ nmr spectra and mass spectra were consistent with the assigned structure.

Preparation 2

2-(2-o-Tolyl-ethyl)-malonic Acid Diethyl Ester 33.9 mL (0.223 mol) of diethyl malonate were added, under a nitrogen atmosphere and at room temperature, to a solution of sodium ethoxide (prepared in situ by dissolving 2.6 g (0.0151 mol) of Na in 80 mL of absolute EtOH). After 30 min, 14.5 g (0.0677 mol) of 2-methylphenethyl alcohol methanesulphonate dissolved in 40 mL of abs. EtOH were added dropwise and the resulting solution was heated to reflux for 3 h. EtOH was removed in vacuo, the residue was taken up in water and extracted with $Et_2O$. The organic phase was washed successively with 10% HCl and brine, dried and the solvent was removed in vacuo. The excess diethyl malonate was removed by distillation under reduced pressure. The resulting oil (15.6 g) was used without further purification.

IR, $^1H$ nmr spectra and mass spectra were consistent with the assigned structure.

Preparation 3

3,3-Bis-ethoxycarbonyl-5-o-tolyl-pentanoic acid tert-butyl Ester

A solution of 7.7 g (0.0277 mol) of 22-o-tolyl-ethyl)-malonic acid diethyl ester in 70 ml of dry THF was added dropwise, under a nitrogen atmosphere at room temperature, to a suspension of 1.4 g (0.036 mol) of NaH (60% dispersion in mineral oil) in 160 mL of dry TH. The reaction mixture was stirred for 30 min, ten 5.3 mL (0.036 mol) of t-butyl bromoacetate were added dropwise. After 3 h the reaction mixture was quenched with water (at 0° C.) and extracted with $Et_2O$. The organic phase was dried, the solvent was removed in vacuo and the residue was purified by flash chromatography, eluting with a mixture Hexane/$Et_2O$ 8:2, yielding 9.3 g of the title compound.

IR, $^1H$ nmr spectra and mass spectra were consistent with the assigned structure.

Preparation 4

3,3-Bis-ethoxycarbonyl-S-o-tolyl-pentanoic Acid 18.7 g (0.0476 mol) of 3,3-bis-ethoxycarbonyl-S-o-tolyl-pentanoic acid tert-butyl ester were dissolved in 40 mL of trifluoroacetic acid and stirred 1 h at room temperature. Trifluoroacetic acid was removed in vacuo, the residue was taken up in water and extracted with $Et_2O$. The organic phase was dried and the solvent was removed in vacuo, yielding 16.8 g of the title compound which was used without further purification IR, $^1H$ nmr spectra and mass spectra were consistent with the assigned structure.

Preparation 5.

(±)-1-Methyl5-oxo-6,7,8,9-tetrahydro-5H-benzocyclohep-tene-7carboxylic Acid 16.8 g (0.0499 mol) of 3,3-bis-ethoxycarbonyl-5-o-tolyl-pentanoic acid were dissolved in 120 mL of $CH_2Cl_2$ under a nitrogen atmosphere. The solution was cooled to 5° C. and 19 mL (0.1498 mol) of oxalyl chloride were added dropwise. After 3 h the volatiles were removed in vacuo, the resulting oil was dissolved in 200 mL of $CH_2Cl_2$ and this solution was added dropwise, at 0° C. and under inert atmosphere, to a suspension of 26.6 g (0.1996 mol) of $AlCl_3$ in 300 mL of $CH_2Cl_2$. The resulting suspension was vigorously stirred overnight, during which time it was allowed to warm to room temperature. Water was added, followed by 1N HCl up to pH 1. The layers were separated, the organic phase was dried and the solvent was removed in vacuo. The resulting crude product was taken up in dioxane (60 mL) and 6N HCl (200 mL) and heated to reflux for 6 h. After cooling, water was added and the reaction mixture was extracted with $Et_2O$. The organic phase was dried, the solvent was removed in vacuo and the resulting crude product was purified by flash chromatography eluting with $Et_2O$, yielding 5.9 g of compound which was triturated in $(i-Pr)_2O$, filtered and dried, yielding 4.33 g of the title product.

IR, $^1H$ nmr spectra and mass spectra were consistent with the assigned structure.

The following compounds were obtained according to procedures described in Preparations 1-5:

(±)-1,4-Dimethyl-S-oxo-6,7,8,9-tetrahydro-5H-benzocyclo-heptene-7-carboxylic acid;

(±)-1-Fluoro-5-oxo-6,7,8,9-tetrahydro-5H-benzocyclohep-tene-7-carboxylic acid, and;

(±)-1-Bromo-5-oxo-6,7,8,9-tetrahydro-5H-benzocycloheptene-7-carboxylic acid.

IR, $^1$H nmr spectra and mass spectra for all the above compounds were consistent with the assigned structures.

Preparation 6

(±)-1-Methoxy-5-oxo-6,7,8,9-tetrahydro-5H-benzocycloheptene-7-carboxylic Acid

A suspension of 0.7 g of (±)-1-methoxy-5-oxo-6,7,8,9-tetrahydro-5H-benzocycloheptene-7-carboxylic acid ethyl ester (prepared as described in Bowman, *Tetrahedron*, 48, 4027, 1992) in 2 mL of 2N NaOH was refluxed for 2 h, then cooled and extracted with Et$_2$O. The aqueous layer was brought to acidic pH with 10% HCl, the precipitate formed was redissolved in Et$_2$O and the organic phase was washed with water and dried. The solvent was removed in vacuo and the resulting residue was purified by flash chromatography, eluting with a mixture CH$_2$Cl$_2$/MeOH 9:1 respectively, yielding 0.41 g of the title compound.

IR and $^1$H nmr spectra were consistent with the assigned structure.

Preparation 7

2-(2,6-Dichloro-phenyl)-4-hydroxy-4-methyl-6-oxo-cyclohexane-13-dicarboxylic Acid Diethyl Ester 20 g (114.3 mmol) of 2,6-dichlorobenzaldehyde and 29 mL (228.6 mmol) of ethyl acetoacetate were dissolved in 40 mL of 96% EtOH; 2 mL of piperidine were added dropwise and the resulting solution was stirred overnight at room temperature. EtOH was removed in vacuo and the resulting residue was crystallised from Et$_2$O, obtaining 25.8 g of the title product IR, $^1$H nmr spectra and mass spectra were consistent with the assigned structure.

Preparation 8

3-(2,6-Dichloro-phenyl)-pentanedioic Acid 25.8 g (61.8 mmol) of 2-(2,6-chloro-phenyl)$_4$-hydroxymethyl-6-oxo-cyclohexane-1,3-dicarboxylic acid diethyl ester were dissolved in 200 mL of 96% EtOH, 150 mL of 35% NaOH solution and 60 mL of H$_2$O; the resulting solution was heated to reflux for 3 h, then the solvent was removed in vacuo and the resulting aqueous solution was carefully acidified at 0° C. with conc. HCl and extracted with AcOEt. The organic solution was dried and the solvent was removed in vacuo. The resulting crude solid was triturated with Et$_2$O, filtered and dried, yielding 14.8 g of the title compound.

IR, $^1$H nmr spectra and mass spectra were consistent with the assigned structure.

Preparation 9

4-(2,6-Dichloro-phenyl)-piperidine-2,6-dione 14.5 g (52 mmol) of 3-(2,6-dichloro-phenyl)-pentanedioic acid were dissolved in 140 mL of conc. NH$_4$OH solution. All the volatiles were removed in vacuo and the resulting solid was heated to 190° C. for 6 h. The crude reaction mixture was taken up in CH$_2$Cl$_2$, the organic phase was washed with 0.1 M Na$_2$CO$_3$ solution, dried and evaporated to dryness. The resulting crude solid was triturate with Et$_2$O, filtered and dried, yielding 9.37 g of the title compound.

IR, $^1$H nmr spectra and mass spectra were consistent with the assigned structure.

Preparation 10

4-(2,6-Dichloro-phenyl)piperidine hydrochloride 9.0 g (34.9 mmol) of 4-(2,6-dichloro-phenyl)-piperidine-2,6-dione were dissolved in 150 mL of dry THF under a nitrogen atmosphere. The resulting solution was cooled to 0° C. and 35 mL (ca 350 mmol) of borane-methylsulphide complex dissolved in 100 mL of dry THF were added dropwise. The reaction mixture was allowed to warm to room temperature, heated to reflux for 3 h, then cooled to −5° C. and quenched by careful addition of 150 mL of 10% HCl solution. The reaction mixture was subsequently heated to reflux for 3 h, then, after cooling, the volatiles were removed in vacuo. The residue was taken up in water, basified with 2 N NaOH solution and extracted with AcOEt The organic phase was dried and the solvent was removed in vacuo. The resulting oil was taken up in CH$_2$Cl$_2$, brought to acidic pH with Et$_2$O/HCl and the solvent was removed in vacuo. The resulting solid was triturated with Et$_2$O, filtered and dried, yielding 7.1 g of the title compound.

IR, $^1$H nmr spectra and mass spectra were consistent with the assigned structure.

The following compounds were obtained according to procedures described in Preparations 7-10:

4-(3-Fluoro-2-methyl-phenyl)piperidine hydrochloride;
4-(2-Chloro-phenyl)piperidine hydrochloride;
4-Phenyl-piperidine hydrochloride;
4-(2-Methyl-phenyl)-piperidine hydrochloride;
4-(2-Fluoro-phenyl)-piperidine hydrochloride;
4-(3-Methyl-phenyl)-piperidine hydrochloride;
4-(2,5-Difluoro-phenyl)-piperidine hydrochloride;
4-(2,6-Difluoro-phenyl)-piperidine hydrochloride;
4-(2-Chloro-6-fluoro-phenyl)-piperidine hydrochloride;
4-(2-Bromo-phenyl)-piperidine hydrochloride, and;
4-(2-Trifluoromethyl-phenyl)-piperidine hydrochloride.

IR, $^1$H nmr spectra and mass spectra for all the above compounds were consistent with the assigned structures.

Preparation 11

1-Benzyl-4-(3,5-dimethyl-phenyl)piperidin-4-ol 5 mL (36.8 mmol) of 5-bromo-m-xylene were dissolved in 40 mL of dry THF under a nitrogen atmosphere. The resulting solution was cooled to −50° C. and 36.5 mL (58.4 mmol) of a 1.6 M solution of n-BuLi in hexane were added dropwise. The reaction mixture was stirred 30 min, then a solution of 10.3 mL (58.4 mmol) of 1-benzyl-4-piperidone in 20 mL of dry THF was added dropwise; stirring was continued for 1 h at −50° C., then the reaction mixture was allowed to warm to room temperature overnight. Water was added carefully and TIF was removed in vacuo; the resulting aqueous solution was extracted with AcOEt, the organic phase was dried and the solvent was removed in vacuo. The resulting crude product was purified by flash chromatography, eluting with a mixture CH$_2$Cl$_2$/MeOH/conc. NH$_4$OH 100:2:0.4 respectively, yielding 5.44 g of the title compound.

IR, $^1$H nmr spectra and mass spectra were consistent with the assigned structure.

Preparation 12

1-Benzyl-4-(3-dimethyl-phenyl)-1,2,3,6-tetrahydropyridine 5.44 g (18.41 mmol) of 1-benzyl-4-(3,5-dimethyl-phenyl)-piperidin-4-ol were dissolved in 7 mL of glacial acetic acid, then a mixture of 3.3 mL of glacial acetic acid and S mL of conc. H$_2$SO$_4$ was added dropwise, keeping the temperature below 0° C. The reaction mixture was allowed to warm to room temperature and stirred 3 h, then it was poured onto 20 g of crushed ice, carefully basified with conc. NaOH solution and extracted with AcOEt. The organic phase was dried and the solvent was removed in vacuo, yielding 4.4 g of the title compound, which was used without further purification.

IR, $^1$H nmr spectra and mass spectra were consistent with the assigned structure.

Preparation 13

4-(3,5-Dimethylphenyl)piperidine 1.24 g of 10% Pd on activated carbon were suspended in 15 mL of water, then a solution of 4.4 g (15.86 mmol) of 1-benzyl-4-(3,5-diethylphenyl)-1,2,3,6-tetrahydropyridine in 60 mL of EtOH was added followed by 1 mL of formic acid The resulting mixture was hydrogenated at 45 p.s.i. in a Parr apparatus for 6 h, then the catalyst was filtered off and the solvent was removed in vacuo. The resulting residue was taken up in water, basified with conc. NH$_4$OH solution and extracted with CH$_2$Cl$_2$. The organic phase was dried and the solvent was removed in vacuo, yielding 2.5 g of the title compound, which was used without further purification.

IR, $^1$H nmr spectra and mass spectra were consistent with the assigned structure.

The following compound was obtained according to procedure described in Preparation 13:

4-(2,6-dimethyl-phenyl)-1,2,3,6-tetrahydropyridine.

IR, $^1$H nmr spectra and mass spectra for the above compound were consistent with the assigned structure.

Preparation 14

4-(2,6-Dimethyl-phenyl)piperidine Hydrochloride 250 mg (35.75 mmol) of lithium wires were added portionwise, under an argon atmosphere at −78° C., to 25 mL of liquid ammonia, then 840 mg (4.47 mmol) of 4-(2,6-dimethylphenyl)-1,2,3,6-tetrahydropyridine dissolved in 15 mL of dry THF were added dropwise. The reaction mixture was stirred 1 h at −78° C., then it was allowed to warm to room temperature. After ammonia has been removed it was cooled to 0° C. and 50 mL of water were added. The reaction mixture was extracted with CH$_2$Cl$_2$, the organic layer was washed with brine, dried and the solvent removed in vacuo. The resulting oily residue was dissolved in CH$_2$Cl$_2$ and brought to acidic pH with Et$_2$O/HCl. The solvent was removed in vacuo and the resulting solid was triturated with (i-Pr)$_2$O, filtered and dried, yielding 790 mg of the title compound.

IR, $^1$H nmr spectra and mass spectra were consistent with the assigned structure.

Preparation 15

4-(2-Hydroxymethyl-phenyl)-1-piperidinecarboxylic acid, 1,1-dimethylethyl Ester 250 mg (0.87 mmol) of 4-(2-formyl-phenyl)-1,2,3,6-tetrahydropyridinecarboxylic acid 1,1-dimethylethyl ester (prepared as described in Wustrow, *Synthesis*, 993, 1991) were dissolved in 35 mL of absolute EtOH. 125 mg of PtO$_2$ were added and the resulting mixture was hydrogenated in a Parr apparatus at 10 p.s.i. for 24 h, then the catalyst was filtered off and the solvent was removed in vacuo, yielding 260 mg of the title compound, which was used without further purification.

IR, $^1$H nmr spectra and mass spectra were consistent with the assigned structure.

Preparation 16

4-(2-Hydroxymethyl-phenyl)piperidine hydrochloride 260 mg (0.89 mmol) of 4-(2-hydroxymethylphenyl)-1-piperidinecarboxylic acid, 1,1-dimethylethyl ester were dissolved in 20 mL of CH$_2$Cl$_2$, 4 mL of a saturated Et$_2$O/HCl solution were added and the reaction mixture was stirred at room temperature for 45 min. The solvent was removed in vacuo and the resulting crude solid was triturated with CH$_2$Cl$_2$, filtered and dried, yielding 180 mg of the title compound.

IR, $^1$H nmr spectra and mass spectra were consistent with the assigned structure.

Preparation 17

(±)-1-Methyl-7-[[4-(2,6-dichlorophenyl)piperidin-1-yl]carbonyl]6,7,8,9-tetrahydro-5H-benzocyclohepten-5-one 1 g (4.58 mmol) of (±)-1-methyl-5-oxo-6,7,8,9-tetrahydro-5H-benzocycloheptene-7-carboxylic acid was dissolved in 40 mL of dry CH$_2$Cl$_2$ and 1.2 mL (13.74 mmol) of oxalyl chloride were added dropwise at 0° C. under a nitrogen atmosphere. The solution was allowed to warm to room temperature overnight, then the solvent and the excess oxalyl chloride were removed in vacuo. The resulting acyl chloride was dissolved in 20 mL of dry CH$_2$Cl$_2$ and added to a solution of 1.22 g (4.58 mmol) of 4-(2,6-dichlorophenyl)-piperidine hydrochloride and 1.91 mL (13.74 mmol) of triethylamine in 30 mL of dry CH$_2$Cl$_2$ at 0° C. The reaction mire was allowed to warm to room temperature overnight, water was added, the organic phase was collected, washed with 1 N HCl solution and dried. The solvent was removed in vacuo and the resulting crude product was purified by flash chromatography, eluting with a mixture Et2O/Hexane 8:2 respectively, yielding 1.4 g of the title compound.

IR, $^1$H nmr spectra and mass spectra were consistent with the assigned structure.

The following compounds were obtained according to procedures described in Preparation 17:

(±)-1-Fluoro-7-[[4-(2-chlorophenyl)piperidin-1-yl]carbonyl]-6,7,8,9-tetrahydro-5H-benzocylohepten-5-one;

(±)-1-Fluoro-7-[[4-(2-methylphenyl)piperidin-1-yl]carbonyl]-6,7,8,9-tetrahydro-5H-benzocylohepten-5-one;

(±)-1-Methyl-7-[[42-fluorophenyl)piperidin-1-yl]carbonyl]-6,7,8,9-tetrahydro-5H-benzocylohepten-5-one;

(±)-1-Methyl-7-[[4-(3-methylphenyl)piperidin-1-ylcarbonyl]-6,7,8,9-tetrahydro-5H-benzocylohepten-5-one;

(±)-1-Methyl-7-[[4-(2-chlorophenyl)piperidin-1-yl]carbonyl]-0.6,7,8,9-tetrahydro-5H-benzocylohepten-5-one;

(±) 1-Bromo-7-[[4-(3-methylphenyl)piperidin-1-yl]carbonyl]-6,7,8,9-tetrahydro-5H-benzocylohepten-5-one;

(±)-1-Bromo-7-[[4-(2-chlorophenyl)piperidin-1-yl]carbonyl]-6,7,8,9-tetrahydro-5H-benzocylohepten-5-one;

(±)-1-Methyl-7-[[4-(2,5-fluorophenyl)piperidin-1-yl]carbonyl]-6,7,8,9-tetrahydro-5H-benzocylohepten-5-one;

(±)-1-Methyl-7-[[s(2,6-fluorophenyl)piperidin-1-yl]carbonyl]-6,7,8,9-tetrahydro-5H-benzocylohepten-5-one;

(±)-1-Methyl-7-[[4-(2-chlorosfluorophenyl)piperidin-1-yl]carbonyl]-6,7,8,9-tetrahydro-5H-benzocyclohepten-5-one;

(±)-1-Methyl-7-[[4-(2-bromophenyl)piperidin-1-yl]carbonyl]-6,7,8,9-tetrahydro-5H-benzocyclohepten-5-one;

(±)-1-Methyl-7-[[4-(2-trifluoromethylphenyl)piperidin-1-yl]carbonyl]-6,7,8,9-tetrahydro-5H-benzocyclohepten-5-one;

(±)-1-Methoxy-7-[(4phenylpiperidin-1-yl)carbonyl]-6,7,8,9-tetrahydro-5H-benzocyclohepten-5-one;

(±)-1-Methoxy-7-[[4-(2-methylphenyl)piperidin-1-yl]arbonyl]-6,7,8,9-tetrahydro-5H-benzocyclohepten-5-one;

(±)-1-Methyl-7-[[4-(3-fluoro-2-methylphenyl)piperidin-1)-yl]carbonyl]-6,7,8,9-tetrahydro-5H-benzocyclohepten-5-one;

(±)-1,4-Dimethyl-7-[[4-(2-methylphenyl)piperidin-1-yl]carbonyl]-6,7,8,9-tetrahydro-5H-benzocyclohepten-5-one;

(±)-1-Methyl-7-[[4-(2,6-dimethylphenyl)piperidin-1-ylcarbonyl]-6,7,8,9-tetrahydro-5H-benzocyclohepten-5-one;
(±)-1-Fluoro-7-[[4-(2,6-dichlorophenyl)piperidin-1-yl]carbonyl]-6,7,8,9-tetrahydro-5H-benzocyclohepten-5-one;
(±)-1-Fluoro-7-[(4,2,6-dimethylphenyl)piperidin-1-yl]carbonyl]-6,7,8,9-tetrahydro-5H-benzocyclohepten-5-one;
(±)-1,4-Diethyl-7-[[4-(2,6-dichlorophenyl)piperidin-1-yl]carbonyl]-6,7,8,9-tetrahydro-5-benzocyclohepten-5-one;
(±)-1-Methyl-7-[[4-(2,6-dimethylphenyl)piperidin-1-yl]carbonyl]-6,7,8,9-tetrahydro-5H-benzocyclohepten-5-one, and;
(±)-1-Methyl-7-[[4-(2-hydroxymethylphenyl)piperidin-1-yl]carbonyl]-6,7,8,9-tetrahydro-5H-benzocyclohepten-5-one.

IR, $^1$H nmr spectra and mass spectra for all the above compounds were consistent with the assigned structures.

Preparation 18

(±)-1-Hydroxy-([4-(2-methylphenyl)piperidin-1-yilcarbonyl]-6,7,8,9-tetrahydro-5H-benzocyclohepten-5-one 780 mg (1.99 mmol) of (±)-1-methoxy-7-[[4-(2-methylphenyl)piperidin-1-yl]carbonyl]-6,7,8,9-tetrahydro-5H-benzocyclohepten-5-one dissolved in 15 mL of $CH_2Cl_2$ were added dropwise, at room temperature and under a nitrogen atmosphere, to a solution of 1.1 mL (11.94 mmol) of $BBr_3$ in 10 mL of $CH_2Cl_2$. The reaction mixture was stirred 2 h at room temperature, then it was poured onto 20 g of crushed ice, basified with conc. $NH_4OH$ and extracted with $CH_2Cl_2$. The organic layer was dried and the solvent was removed in vacuo. The resulting crude solid was triturated with $Et_2O$, filtered and dried, yielding 600 mg of the title compound.

IR, $^1$H nmr spectra and mass spectra were consistent with the assigned structure.

Preparation 19

(±)-1-Trifluoromethanesulfonyloxy-7-[[4-(2-methylphenylpiperidin-1-yl]carbonyl]-6,7,8,9-tetrahydro-5H-benzocyclohepten-5-one 600 mg (1.59 mmol) of (+1-hydroxy-7-[[4-(2-methylphenyl)piperidin-1-yl]carbonyl]-6,7,8,9-tetrahydro-5H-benzocyclohepten-5-one were dissolved in 5 mL of pyridine under a nitrogen atmosphere and 0.294 mL (1.75 mmol) of trifluoromethanesulfonic anhydride were added dropwise at −5° C. The reaction mixture was allowed to warm to room temperature after 5 min and stirred overnight, then it was poured in water, acidified with 20% citric acid solution and extracted with AcOEt The organic layer was dried and the solvent was removed in vacuo. The resulting residue was purified by flash chromatography, eluting with $Et_2O$, yielding 520 mg of the title compound.

IR, $^1$H nmr spectra and mass spectra were consistent with the assigned structure.

Preparation 20

(±)-1-Vinyl-7-[[4-(2-methylphenyl)piperidin-1-yl]carbonyl]-6,7,8,9-tetrahydro-5H-benzocyclohepten-5-one 510 mg (1 mmol) of (±)-1-trifluoromethanesulfonyloxy-7-[[4-(2-methylphenyl)piperidin-1-yl]carbonyl]-6,7,8,9-tetrahydro-5H-benzocyclohepten-5-one were dissolved in 4 mL of DMF under an argon atmosphere, then 72 mg (0.1 mmol) of dichlorobis(triphenylphosphine)palladium (II), 340 mg (8 mmol) of LiCl and 105 mg (0.4 mmol) of triphenylphosphine were added, followed by a solution of 0.3 mL (1.04 mmol) of tributyl(vinyl)tin in 0.5 mL of DMF. The reaction mixture was heated to 100° C. for 6 h, then it was poured into water and extracted with AcOEt. The organic layer was dried and the solvent was removed in vacuo. The crude reaction mixture was purified by flash chromatography, eluting with a mixture AcOEt/hexane 1:1, yielding 90 mg of the title compound.

IR, $^1$H nmr spectra and mass spectra were consistent with the assigned structure.

The following compound was obtained according to procedure described in Preparation 20: (±)-1-Allyl-7-[[4-(2-methylphenyl)piperidin-1-yl]carbonyl]-6,7,8,9-tetrahydro-5H-benzocyclohepten-5-one.

IR, $^1$H nmr spectra and mass spectra for the above compound were consistent with the assigned structure.

Preparation 21

(±)-1-Ethyl-7-[[4-(2-methylphenylpiperidin-1-yl]carbonyl]-6,7,8,9-tetrahydro-5H-benzocyclohepten-5-ol 100 mg of 10% Pd on activated carbon were suspended in 10 mL of water, then a solution of 272 mg (0.7 mmol) of (±)-1-vinyl-7-[[4-(2-methylphenyl)piperidin-1-yl]carbonyl]-6,7,8,9-tetrahydro-5H-benzocyclohepten-5-one in 50 mL of EtOH was added, followed by 2 mL of formic acid. The resulting mixture was hydrogenated at 45 p.s.i. in a Parr apparatus for 7 h, then the catalyst was filtered off and the solvent was removed in vacua. The resulting residue was taken up in $CH_2Cl_2$ and extracted with water. The organic phase was dried and the solvent was removed in vacuo, yielding 168 mg of the title compound, which was used without further purification.

IR, $^1$H nmr spectra and mass spectra were consistent with the assigned structure.

Preparation 22.

(±)-1-Methoxy-7-[(phenylpiperidin-1-yl)methyl]-7,8,9-tetrahydro-5H-benzocyclohepten-5one 0.17 mL of the Jones reagent (prepared by mixing 2.67 g of Cr and 2.3 mL of conc. $H_2SO_4$ and adding water up to a final volume of 10 mL) were added to a solution of 0.2 g of (±)-1-methoxy-7-[(4phenylpiperidin-1-yl)methyl]-6,7,8,9-tetrahydro-5H-benzocyclohepten-5-ol in 13 mL of acetone. The solution was stirred at room temperature for 1 h, then the solvent was removed in vacuo, the residue was taken up in water, brought to basic pH with 10% NaOH and extracted with $CH_2Cl_2$. The organic phase was dried and the solvent was removed in vacuo, obtaining 0.15 g of the title compound, which was used without further purification.

IR and $^1$H nmr spectra were consistent with the assigned structure.

EXAMPLE 1

(±)-cis-1-Methyl-7-[142-fluorophenyl)piperidin-1-yl]methyl]-6,7,8,9-tetrahydro-5H-benzocyclohepten-5-ol hydrochloride 380 mg (1 mmol) of (±)-1-methyl-7-[[4-(2-fluorophenyl) piperidin-1-yl]carbonyl]-6,7,8,9-tetrahydro-5H-benzocyclohepten-5-one dissolved in 5 mL of dry THF were added dropwise, at 0° C. and under a nitrogen atmosphere, to 5 mL of a 1 M solution of $LiAlH_4$ in TBF. The reaction mixture was allowed to warm to room temperature and then heated to reflux for 3 h. After cooling to 0° C., the reaction mixture was quenched by sequential addition of water, 15% NaOH solution and water. After stirring for 1 h, the resulting precipitate was filtered by suction and the filtrate was evaporated to dryness. The resulting crude product was purified by chromatography, eluting with a mixture $CH_2Cl_2$/MeOH/conc. $NH_4OH$ 95:4:0.5 respectively, yielding 60 mg of compound which was dissolved in $Et_2O$ and brought to acidic pH with Et₂O/HCl. The solvent was removed in vacuo and the resulting solid was triturate with acetone, filtered and dried, yielding 58 mg of the title compound. m.p.=235–240° C. IR (KBr, cm$^{-1}$)=3435, 2927, 1492. NMR (free base, 400 MHz, CDCl$_3$, δ ppm): 7.43 (d, 1H); 7.29–6.97 (m, 6H); 5.04 (d, 1H); 3.13 (dd, 1H); 3.03–2.92 (m, 2H); 2.86 (m, 1H); 2.47 (dd, 1H); 2.33 (s, 3H); 2.24 (d, 1H); 2.17–2.00 (m, 6H); 1.85–1.74 (m, 5H); 1.31 (m, 1H); 0.88 (m, 1H). MS (m/z): 368 (MH+).

EXAMPLE 2

(±)-1-Methyl-7-[[4-(2-trifluoromethylphenyl)piperidin-1-yl]methyl]-6,7,8,9-tetrahydro-5H-benzocyclohepten-5-ol trifluoroacetate The title compound was obtained according to the method described in Example 1, but it was purified by flash chromatography on Lichrosolv RP 18 stationary phase, by gradient elution with a solvent system water/MeCN/TFA 900:100:0.5 respectively and water/MeCN/TFA 100:900:0.5 respectively, in a 1:3 relative ratio, yielding 20 mg of the title compound NMR (free base, 400 Mz, CDCl$_3$, δ ppm): 7.61 (d, 1H); 7.50 (m, 2H); 7.43 (d, 1H); 7.28 (m, 1H); 7.14 (dd, 1H); 7.07 (d, 1H); 5.04 (d, 1H); 3.14 (dd, 1H); 3.04–2.85 (m, 3H); 2.47 (dd, 1H); 2.33 (s, 3H); 2.30–2.00 (m, 7H); 1.89–1.71 (m, 5H); 1.34 (m, 1H); 0.89 (m, 1H). MS (m/z): 418 (MH+).

Compounds of formula (I) and described in Table 1 were obtained following procedure described in Example 1

TABLE 1

| Ex No. | Name | R | R¹ | R² | R³ | R⁴ | R⁵ | m.p. (° C.) | IR (cm$^{-1}$) | NMR (400 MHz, δ ppm, free base) | MS (m/z) |
|---|---|---|---|---|---|---|---|---|---|---|---|
| 3 | (±)-cis-1-fluoro-7-[[4-(2-chlorophenyl)piperidin-1-yl]methyl]-6,7,8,9-tetrahydro-5H-benzocyclohepten-5-ol hydrochloride | F | H | OH | H | 2-Cl | H | 245–247 | (KBr); 3262, 2932, 1579 | CDCl$_3$: 7.37–7.09(m, 6H); 6.92(t, 1H); 4.97(d, 1H); 3.35(dd, 1H); 3.07–2.91(m, 3H); 2.39–2.21(m, 2H); 2.20–2.00(m, 6H); 1.88–1.65(m, 5H); 1.36(m, 1H); 0.93(m, 1H). | 388 (MH+) |
| 4 | (±)-1-fluoro-7-[[4-(2-methylphenyl)piperidin-1-yl]methyl]-6,7,8,9-tetrahydro-5H-benzocyclohepten-5-ol hydrochloride | F | H | OH | H | 2-Me | H | 231–233 | (KBr); 3297, 2927, 1582 | CDCl$_3$: 7.36(d, 1H); 7.28–7.06(m, 5H); 6.92(t, 1H); 4.97(d, 1H); 3.35(dd, 1H); 3.07–2.92(m, 2H); 2.70(m, 1H); 2.38–2.23(m, 2H); 2.34(s, 3H); 2.20–1.99(m, 6H); 1.87–1.65(m, 5H); 1.37(m, 1H); 0.93(m, 1H). | 367 (M+.); 188; 117; 70 |
| 5 | (±)-cis-1-methyl-7-[[4-(3-methylphenyl)piperidin-1-yl]methyl]-6,7,8,9-tetrahydro-5H-benzocyclohepten-5-ol hydrochloride | Me | H | OH | H | 3-Me | H | >250 | | IR, 1H nmr spectra and mass spectra were consistent with the assigned structure. | |
| 6 | (±)-cis-1-methyl-7-[[4-(2-chlorophenyl)piperidin-1-yl]methyl]-6,7,8,9-tetrahydro-5H-benzocyclohepten-5-ol hydrochloride | Me | H | OH | H | 2-Cl | H | >250 | (KBr); 3411, 2925, 1441 | CDCl$_3$: 7.42(d, 1H); 7.34(dd, 1H); 7.29(dt, 1H); 7.23(dt, 1H); 7.16–7.09(m, 2H); 7.06(d, 1H); 5.04(d, 1H); 3.14(dd, 1H); 3.07–2.93(m, 3H); 2.47(dd, 1H); 2.33(s, 3H); 2.24(d, 1H); 2.19–2.02(m, 6H); 1.87–1.69(m, 5H); 1.31(m, 1H); 0.88(m, 1H). | 383 (M+.); 208 |
| 7 | (±)-cis-1-methyl-7-[[4-(2,5-difluorophenyl)piperidin-1-yl]methyl]-6,7,8,9-tetrahydro-5H-benzocyclohepten-5-ol hydrochloride | Me | H | OH | H | 2-F | 5-F | — | — | CDCl$_3$: 7.42(d, 1H); 7.14(dd, 1H); 7.06(d, 1H); 6.99–6.90(m, 2H); 6.87–6.79(m, 1H); 5.04(d, 1H); 3.13(dd, 1H); 3.03–2.91(m, 2H); 2.88–2.77(m, 1H); 2.46(dd, 1H); 2.32(s, 3H); 2.26–2.00(m, 7H); 1.81–1.68(m, 5H); 1.38–1.24(m, 1H); 0.87(m, 1H). | 385 (M+.); 210 |
| 8 | (±)-cis-1-methyl-7-[[4-(2,6-difluorophenyl)piperidin-1-yl]methyl]-6,7,8,9-tetrahydro-5H-benzocyclohepten-5-ol hydrochloride | Me | H | OH | H | 2-F | 6-F | — | — | CDCl$_3$: 7.43(d, 1H); 7.13(dd, 1H); 7.08(m, 1H); 7.06(d, 1H); 6.83(d, 1H); 6.80(d, 1H); 5.04(d, 1H); 3.13(dd, 1H); 3.03–2.91(m, 3H); 2.46(dd, 1H); 2.33(s, 3H); 2.29–1.97(m, 9H); 1.7 1–1.62(m, 3H); 1.38–1.24(m, 1H); 0.87(m, 1H). | 385 (M+.); 210 |
| 9 | (±)-cis-1-vinyl-7-[[4-(2-methylphenyl)piperidin-1-yl]methyl]-6,7,8,9-tetrahydro-5H-benzocyclohepten-5-ol hydrochloride | Vinyl | H | OH | H | 2-Me | H | — | — | (CDCl$_3$): 7.53(d, 1H); 7.32(d, 1H); 7.26–7.01(m, 6H); 5.52(dd, 1H); 5.30(dd, 1H); 5.05(d, 1H); 4.80(s br, 1H); 3.24(dd, 1H); 2.98(m, 2H); 2.69(m, 1H); 2.49(dd, 1H); 2.34(s, 3H); 2.28–1.93(m, 6H); 1.85–1.66(m, 5H); 1.33(m, 1H); 0.89(m, 1H). | 376 (MH+) |
| 10 | (±)-cis-1-allyl-7-[[4-(2-methylphenyl)piperidin-1-yl]methyl]-6,7,8,9-tetrahydro-5H-benzocyclohepten-5-ol hydrochloride | Allyl | H | OH | H | 2-Me | H | — | — | (CDCl$_3$): 7.48(d, 1H); 7.25(d, 1H); 7.21–7.04(m, 5H); 5.96(ddt, 1H); 5.03(m, 2H); 4.95(ddt, 1H); 3.43(m, 2H); 3.12(dd, 1H); 2.99(m, 2H); 2.69(m, 1H); 2.44(dd, 1H); 2.33(s, 3H); 2.24(d, 1H); 2.17–1.99(m, 6H); 1.83–1.68(m, 5H); 1.34(m, 1H); 0.85(m, 1H). | 389 (M+.); 188; 117 |
| 11 | (±)-cis-1-methyl-7-[[4-(3-fluoro-2-methylphenyl)piperidin-1-yl]methyl]-6,7,8,9-tetrahydro-5H-benzocyclohepten-5-ol hydrochloride | Me | H | OH | H | 2-Me | 3-F | — | — | (CDCl$_3$): 7.43(d, 1H); 7.16–7.02(m, 4H); 6.86(dd, 1H); 5.04(d, 1H); 3.13(dd, 1H); 2.99(m, 2H); 2.70(m, 1H); 2.46(dd, 1H); 2.33(s, 3H); 2.26–2.01(m, 7H); 2.23(d, 3H); 1.84–1.68(m, 5H); 1.33(m, 1H); 0.88(m, 1H). | 381 (M+.); 206; 70 |

TABLE 1-continued

| Ex No. | Name | R | R¹ | R² | R³ | R⁴ | R⁵ | m.p. (° C.) | IR (cm⁻¹) | NMR (400 MHz, δ ppm, free base) | MS (m/z) |
|---|---|---|---|---|---|---|---|---|---|---|---|
| 12 | (±)-trans-1-ethyl-7-[[4-(2-methylphenyl)piperidin-1-yl]methyl]-6,7,8,9-tetrahydro-5H-benzocyclohepten-5-ol hydrochloride | Et | H | OH | H | 2-Me | H | — | — | CDCl₃: 7.25(d, 2H); 7.19–7.05(m, 5H); 5.03(m, 1H); 3.13–2.87(m, 4H); 2.68(m, 3H), 2.33(s, 3H); 2.27–1.97(m, 8H); 1.87–1.69(m, 4H); 1.52(m, 2H); 1.17(t, 3H). | 377 (M+.); 188 |
| 13 | (±)-trans-1,4-dimethyl-7-[[4-(2-methylphenyl)piperidin-1-yl]methyl]-6,7,8,9-tetrahydro-5H-benzocyclohepten-5-ol | Me | 4-Me | OH | H | 2-Me | H | — | — | (CDCl₃, 333 K): 7.25(d, 1H); 7.20–7.05(m, 3H); 6.98(d, 1H); 6.91(d, 1H); 5.34(t. 1H); 3.20(m, 1H); 3.00(m, 2H); 2.78(m, 1H); 2.69(m, 1H); 2.41(s, 3H); 2.32(s, 3H); 2.28(s, 3H); 2.23–1.96(m, 6H); 1.96–1.54(m, 7H); 1.02(m, 1H). | 378 (MH+) |
| 14 | (±)-cis-1-methyl-7-[[4-(2,6-dimethylphenyl)piperidin-1-yl]methyl]-6,7,8,9-tetrahydro-5H-benzocyclohepten-5-ol hydrochloride | Me | H | OH | H | 2-Me | 6-Me | — | — | (CDCl₃): 7.43(d, 1H); 7.14(dd, 1H); 7.06(d, 1H); 6.98(s, 3H), 5, 11(s br, 1H); 5.03(d, 1H); 3.13(dd, 1H); 2.98(m, 3H); 2.46(dd, 1H); 242(s br, 6H); 2.33(s, 3H); 2.25(m, 4H); 2.15–1.95(m, 6H); 1.39–1.15(m, 2H); 0.86(m, 1H). | 377 (M+.); 202 |
| 15 | (±)-cis-1-fluoro-7-[[4-(2,6-dimethylphenyl)piperidin-1-yl]methyl]-6,7,8,9-tetrahydro-5H-benzocyclohepten-5-ol hydrochloride | F | H | OH | H | 2-Me | 6-Me | — | — | (CDCl₃): 7.36(d, 1H); 7.18(m, 1H); 6.97(s, 3H); 6.92(dd, 1H); 4.97(d, 1H); 3.35(dd, 1H); 2.98(m, 3H); 2.42(s br, 6H); 2.40–1.97(m, 11H); 1.58(m, 2H); 1.35 (m, 1H); 0.91(m, 1H). | 382 (MH+) |
| 16 | (±)-1,4-dimethyl-7-[[4-(2,6-dimethylphenyl)piperidin-1-yl]methyl]-6,7,8,9-tetrahydro-5H-benzocyclohepten-5-ol hydrochloride | Me | 4-Me | OH | H | 2-Me | 6-Me | — | — | (CDCl₃): 6.97(d, 1H); 6.96(s, 3H); 6.92(d, 1H); 5.32(t, 1H); 3.19(m, 1H); 3.00–2.89(m, 3H); 2.77(m, 1H); 2.42(s br, 9H); 2.42–2.19(m, 4H); 2.28(s, 3H); 2.07(m, 2H); 1.89(m, 1H); 1.73(m, 3H); 1.65–1.53(m, 4H). | 392 (MH+) |
| 17 | (±)-cis-1-methyl-7-[[4-(2-hydroxymethylphenyl)piperidin-1-yl]methyl]-6,7,8,9-tetrahydro-5H-benzocyclohepten-5-ol | Me | H | OH | H | 2-CH₂OH | H | — | — | (CDCl₃): 7.38(d, 1H); 7.30(d, 1H); 7.24(d, 1H); 7.18(dd, 1H); 7.10(dd, 1H); 7.03(dd, 1H); 6.96(d, 1H); 4.92(d, 1H); 4.64(d, 2H); 3.09–2.83(m, 5H); 2.76(m, 1H); 2.38(dd, 1H); 2.,23(s, 3H); 2.22–1.91(m, 7H); 1.80–1.61(m, 4H); 1.20(m, 1H); 0.77(m, 1H). | 379 (M+.); 204; 167 |

EXAMPLE 18

(±)-cis-1-Methyl-7-[[(2chloro-6-fluorophenyl)piperidin-1-yl]methyl]-6,7,8,9-tetrahydro-5H-benzocyclohepten-5-ol hydrochloride 3.0 mL of a 1 M solution of diisobutylaluminium hydride in hexane were added dropwise, at 0° C. and under a nitrogen atmosphere, to a solution of 350 mg (0.85 mmol) of (±)-1-methyl-7-[[4-(2-chloro-6-fluorophenyl)piperidin-1-yl]carbonyl]-6,7,8,9-tetrahydro-5H-benzocyclohepten-5-one in 6 mL of dry THF. The reaction mixture was allowed to warm to room temperature overnight, then it was poured onto 20 mL of a saturated solution of sodium potassium tartate tetrahydrate; 1 mL of 15% NaOH solution was added and the aqueous phase was extracted with Et₂O. The organic phase was dried and the solvent was removed in vacua. The crude product was purified by flash chromatography, eluting with a mixture CH₂Cl₂/MeOFconc. NH₄OH 100:4:0.1 respectively, yielding 25 mg of compound which was dissolved in Et₂O and brought to acidic pH with Et₂O/HCl. The solvent was removed in vacuo and the resulting solid was triturate with acetone, filtered and dried, yielding 15 mg of the title compound.

NMR (free base, 400 MHz, CDCl₃, δ ppm): 7.43 (d, 1H); 7.16-7.04 (m, 4H); 6.93 (ddd, 1H); 5.03 (d, 1H); 3.20–3.10 (m, 2H): 3.02-2.92 (m, 2H); 2.46 (dd, 1H); 2.29–1.97 (m, 9H); 1.70–1.62 (m, 3H); 1.32 (m, 1H): 0.86 (m, 1H). MS (m/z): 401 (M+.); 226; 210.

EXAMPLE 19

(±)-1-Bromo-7-[[(2-chlorophenyl)piperidin-1-yl]methyl]-6,7,8,9-tetrahydro-5H-benzocyclohepten-5-ol Trifluoroacetate The title compound was obtained according to the method described in Example 18, but it was purified by preparative HPLC on a Supelcosil ABZ+plus column, by gradient elution with a solvent system water/MeCNITFA 900:100:0.5 respectively (A) and water/MeCN/TFA 100:900:0.5 respectively (B), with a gradient from 0% B to 80% (B) in 19 min., yielding 14 mg of the title compound.

NMR (free base, 400 MHz, CDCl₃, δ ppm): 7.48 (dd, 1H); 7.367.18 (m, 4H); 7.12 (dd, 1H); 7.00 (dd, 1H); 5.03 (m, 1H); 3.35–3.13 (m, 1H); 3.05–2.93 (m, 2H); 2.26–2.02 (m, 8H); 1.87–1.70 (m, 6H); 1.58 (m, 1H); 1.26 (m, 1H). MS (m/z): 448 (MH+).

Compounds of formula (I) and described in Table 2 were obtained following procedure described in Example 18

TABLE 2

| Ex No. | Name | R | R¹ | R² | R³ | R⁴ | R⁵ | m.p. (°C.) | IR (cm⁻¹) | NMR (400 MHz, δ ppm, free base) | MS (m/z) |
|---|---|---|---|---|---|---|---|---|---|---|---|
| 20 | (±)-trans-1-bromo-7-[[4-(3-methylphenyl)piperidin-1-yl]methyl]-6,7,8,9-tetrahydro-5H-benzocyclohepten-5-ol hydrochloride | Br | H | OH | H | 3-Me | H | >250 | (KBr); 3326, 2959, 1446 | CDCl$_3$: 7.47(dd, 1H); 7.23(d, 1H), 7.17(d, 1H); 7.05–6.97(m, 4H); 5.02(m, 1H); 3.33–3.14(m, 2H); 3.01–2.93(m, 2H); 2.49–2.38(m, 1H); 2.33(s, 3H); 2.25–1.92(m, 7H); 1.83–1.74(m, 5H); 1.54(m, 1H); 1.22(m, 1H). | 427 (M+.); 188 |
| 21 | (±)-cis-1-methyl-7-[[4-(2-bromophenyl)piperidin-1-yl]methyl]-6,7,8,9-tetrahydro-5H-benzocyclohepten-5-ol | Me | H | OH | H | 2-Br | H | — | — | CDCl$_3$: 7.53(d, 1H); 7.42(d, 1H); 7.307.24(m, 2H); 7.13(dd, 1H); 7.06(d, 1H); 7.04(m, 1H); 5.04(d, 1H); 3.13(dd, 1H); 3.05–2.90(m, 3H); 2.47(dd, 1H); 3.33(s, 3H); 2.29–2.01(m, 8H); 1.88–1.64(m, 4H); 1.34(m, 1H); 0.88(m, 1H). | 428 (M+.); 252; 242; |

EXAMPLE 22

(±)-cis-1-Methyl-7-[[4-(2,6-dichlorophenyl)piperidin-1-yl]methyl]6,7,8,9-tetrahydro-5H-benzocyclohepten-5-ol Hydrochloride A solution of 1076 mg (8.06 mmol) of AlCl$_3$ in 50 mL of dry Et$_2$O was added dropwise, at 0° C. and under a nitrogen atmosphere, to a suspension of 275 mg (7.25 mmol) of LiAlH$_4$ in 50 mL of dry Et$_2$O. The resulting mixture was stirred for 10 min., then 828 mg (1.92 mmol) of (±)-1-methyl-7-[[4-(2,6-dichlorophenyl)piperidin-1-yl]carbonyl]-6,7,8,9-tetrahydro-5H-benzocyclohepten-5-one dissolved in 50 mL of dry Et$_2$O were added dropwise. The reaction mixture was allowed to warm to room temperature and stirred 4 h, then it was cooled to 0° C. and quenched with water, 15% NaOH solution and water. The aqueous phase was extracted with Et$_2$O, the organic phase was dried and the solvent was removed in vacuo. The crude product was purified by flash chromatography, eluting with a mixture CH$_2$Cl$_2$/i-PrOH/conc. NH$_4$OH 100:2:0.1 respectively, yielding 200 mg of the cis diastereoisomer as the faster eluting compound 45 mg of free base were dissolved in CH$_2$Cl$_2$, the solution was brought to acidic pH with Et$_2$O/HCl and the solvent was removed in vacuo. The resulting solid was triturated with acetone, filtered and dried, yielding 40 mg of the title compound. m.p.=235–240° C. IR (KBr, cm⁻¹) =3435, 2963, 1436, 1261, 1095. NMR (free base, 400 MHz, CDCl$_3$, δ ppm): 7.42 (d, 1H); 7.29–7.23 (m, 2H); 7.12 (dd, 1H); 7.05 (d, 1H); 7.01 (dd, 1H); 5.03 (d, 1H); 3.52 (tt, 1H); 3.16 (dd, 1H); 3.042.94 (m, 2H); 2.74–2.58 (m, 2H); 2.50 (dd, 1H); 2.34 (s, 3H); 2.27 (m, 1H); 2.19–2.03 (m, 6H); 1.59–1.40 (m, 31H); 1.32 (m, 1H); 0.90 (m, 1H). MS (m/z): 418 (MH+)

EXAMPLE 23

(±)-trans-1-Methyl-7-[[4-(2,6-dichlorophenyl)piperidin-1-yl]methyl]6,7,8,9-tetrahydro-5H-benzocyclohepten-5ol The chromatography of the preceding example was continued, obtaining 50 mg of the trans diastereoisomer as the slower eluting compound.

NMR (400 MHz, CDCl, δ ppm): 7.30–7.25 (m, 2H); 7.147.00 (m,4H); 5.02 (m, 1H); 3.48 (tt, 1H); 3.11–2.87 (m, 4H); 2.71–2.55 (m, 2H); 2.34 (s, 31); 2.31–1.99 (m, 8H); 1.51 (m, 3H); 1.17 (m, 1H). MS (m/z): 418 (MH+).

Compounds of formula (I) and described in Table 3 were obtained following procedure described in Example 22

TABLE 3

| Ex No. | Name | R | R¹ | R² | R³ | R⁴ | R⁵ | m.p. (°C.) | IR (cm⁻¹) | NMR (400 MHz, δ ppm, free base) | MS (m/z) |
|---|---|---|---|---|---|---|---|---|---|---|---|
| 24 | (±)-cis-1-fluoro-7-[[4-(2,6-dichlorophenyl)piperidin-1-yl]methyl]-6,7,8,9-tetrahydro-5H-benzocyclohepten-5-ol hydrochloride | F | H | OH | H | 2-Cl | 6-Cl | — | — | (CDCl$_3$): 7.36(d, 1H); 7.27(m, 1H); 7.18(m, 1H); 7.04(d, 1H); 7.02(d, 1H); 6.92(dd, 1H); 4.96(d, 1H); 3.49(tt 1H); 3.35(dd, 1H); 2.98(m, 2H); 2.64(dq, 2H); 2.38–2.00(m, 9H); 1.54(m, 2H); 1.35(m, 1H); 0.91(m, 1H). | 422 (MH+); |
| 25 | (±)-1,4-dimethyl-7-[[4-(2,6-dichlorophenyl)piperidin-1-yl]methyl]-6,7,8,9-tetrahydro-5H-benzocyclohepten-5-ol | Me | 4-Me | OH | H | 2-Cl | 6-Cl | — | — | (CDCl$_3$): 7.25(m, 2H); 7.02(dd, 1H); 6.98(d, 1H); 6.92(d, 1H); 5.33(dd, 1H); 3.47(tt, 1H); 3.18(dd, 1H); 2.96(m, 2H); 2.78(m, 1H); 2.64(m, 2H); 2.42(s, 3H); 2.42–2.26(m, 4H); 2.28(s, 3H); 2.17–2.00(m, 3H); 1.84–1.47(m, 5H). | 432 (MH+) |

Racemic (±)-cis-1-methyl-7-[[4-(2,6-dichlorophenyl)piperidin-1-yl]methyl]-6,7,8,9-tetrahydro-5H-benzocyclohepten-5-ol (compound of Example 22) was separated by preparative HPLC on chiral stationary phase (Daicel Chiralcel OD, elution with 95:5 Hexane:Ethanol, 17 mL/min), obtaining:

EXAMPLE 26

(±)-cis-1-Methyl-7-[[4-(2,6-dichlorophenyl)piperidin-1-yl]methyl]-6,7,8,9-tetrahydro-5H-benzocyclohepten-5-ol The title compound was obtained with e.e.>99.8% (HPLC). [α]$^{20}_D$=−30.7 (c=0.5, i-PrOH). $^1$H NMR matched that of the racemate.

EXAMPLE 27

(±)-cis-1-Methyl-7-[[4-(2,6-dichlorophenyl)piperidin-1-yl]methyl]-6,7,8,9-tetrahydro-5H-benzocyclohepten-5-ol The title compound was obtained with e.e.>99.8% (HPLC). [a]$^{20}_D$=+32.6 (c=0.5, i-PrOH). $^1$H NMR matched that of the racemate.

EXAMPLE 28

(±)-1-Methoxy-5methyl-7-[(4-phenylpiperidin-1-yl)methyl]6,7,8,9-tetrahydro-5H-benzocyclohepten-5-ol hydrochloride A solution of 140 mg (0.38 mmol) of (±)-1-methoxy-7-[(4phenylpiperidin-1-yl)methyl]-6,7,8,9-tetrahydro-5H-benzocyclohepten-5-one in 5 mL of dry Et$_2$O was added, at 0° C. and under a nitrogen atmosphere, to 1 mL of a 3 M MeMgI solution in Et$_2$O. The reaction mixture was stirred 1 h at 0° C., then allowed to warm to room temperature and stirred an additional hour, then it was cooled to 0° C. and quenched with saturated NH$_4$Cl solution. The aqueous phase was extracted with Et$_2$O, the organic phase was collected, dried and the solvent was removed in vacuo. The crude product was purified by flash chromatography, eluting with a mixture toluene/MeOH 9:1 respectively, yielding 40 mg of free base, which was dissolved in Et$_2$O, the solution was brought to acidic pH with Et$_2$O/HCl and the solvent was removed in vacuo. The resulting solid was triturated with Et$_2$O, filtered and dried, yielding 30 mg of the title product m.p.=158–160° C.

$^1$H nmr spectra was consistent with the assigned structure.

Method of Nociceptin Binding Assay

Receptor Cloning and Expression

ORL-1 receptor was stably expressed in a Chinese Hamster Ovary (CHO) cell line (ACC-317) using a pCDN vector. Subclone selection was performed by growth in the absence of nucleosides. The cell line expressing high numbers of ORL-1 binding sites was selected for further characterization in radioligand binding and signal transduction assay (cAMP and GTPgS assays).

Cell Growth Conditions

CHO cells are grown in suspension, in 1017 SO$_3$ culture and maintained at 37° C. and 5% CO$_2$. The cells are routinely grown on a shaker in the presence of 0.05% (v/v) pluronic acid (F68). The maximum cell density for this CHO cell lines is 4×106 cells/ml. The cultures are passed twice a week at a 1:5 or 1:10 dilution.

Membrane Preparation by Hypotonic Lysis

All steps are performed at 4° C.
1) Harvest cells in PBS (approximately 30×10$^6$ cells/tube). Collect cells by centrifugation (1200 rpm, ca 800×g 5 min).
2) Resuspend each pellet in 10 mM dibasic phosphate buffer, pH 7.2 (buffer A)-circa 30 ml/pellet. Centrifuge 15000 rpm 10 min (Sorvall SS-34 rotor).
3) Resuspend the pellets in the same volume of buffer A, incubate on ice for 20 min. Centrifuge at 1200 rpm, 5 min and save the supernatants.
4) Resuspend the low speed pellets in buffer A again and repeat step 3) two more times saving the supernatants each time.
5) Pool the low speed supernatants. Spin (15000 rpm, 10 min) to collect the membranes.
6) Resuspend the pellets in buffer A containing 0.32 M sucrose and S mM EDTA (buffer B). Pool, spin again at high speed to concentrate the membranes and wash in this storage buffer.
7) Resuspend in buffer B the final pellet to a final concentration of 5–10 mg protein/ml (ca 10×10$^6$ cells/ml). Freeze the aliquots at −80° C.

Radioligand Binding

Radioligand binding experiments have been performed in Tris buffer pH 7.4 containing 100 ug/ml Bacitracine, 4 ug/ml Leupeptine and 2 ug/ml Chymostatine at the final volume of 1 ml, using [$^3$H]-Nociceptin (Amersham, 172 Ci/mmol) as the radioligand.

Binding experiments were carried out at 25° C. for 20 min and the reaction was terminated by filtration through Whatman GF/B filters pretreated with 0.2% PEI. Filters were washed 3 times in Tris buffer pH 7.4 at 4° C. The radioactivity present on the discs was measured by liquid scintillation counting using a 2500 Canberra Packard beta counter.

The most potent compounds in accordance with the present invention have an ORL-1 binding affinity (Ki) in the range from 0.1 to 500 nNM.

What is claimed is:

1. A compound of formula (I)

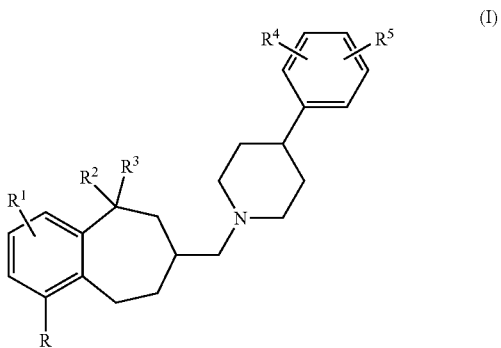

or a derivative thereof,
wherein;
R is $C_{1-6}$alkyl, $C_{3-7}$cycloalkyl, $C_{1-6}$alkoxy, hydroxy, halo, $C_{1-6}$alkenyl, $C_{1-6}$alkynyl, amino, $C_{1-6}$alkylamino, di($C_{1-6}$alkyl)amino, hydroxy$C_{1-6}$alkyl, $C_{1-6}$alkoxy$C_{1-6}$alkyl, amino$C_{1-6}$alkyl, ($C_{1-6}$alkyl)amino$C_{1-6}$alkyl, di($C_{1-6}$alkyl)amino$C_{1-6}$alkyl;
$R^1$ is hydrogen or R;
$R^2$ is hydroxy, $C_{1-6}$alkoxy, amino, $C_{1-6}$alkylamino, di($C_{1-6}$alkyl)amino;
$R^3$ is hydrogen or $C_{1-6}$alkyl;
$R^4$ and $R^5$ are each independently selected from the list consisting of perhalo$C_{1-6}$alkyl, hydrogen, halo, $C_{1-6}$alkyl, $C_{1-6}$alkoxy, hydroxy, amino, $C_{1-6}$alkylamino, di($C_{1-6}$alkyl)amino, hydroxy$C_{1-6}$alkyl, $C_{1-6}$alkoxy$C_{1-6}$alkyl, amino$C_{1-6}$alkyl, ($C_{1-6}$alkyl)amino$C_{1-6}$alkyl, di($C_{1-6}$alkyl)amino$C_{1-6}$alkyl, aryl, and COX wherein X may be hydroxy, $C_{1-6}$ alkoxy, $C_{1-6}$alkyl, amino, $C_{1-6}$alkylamino, or di($C_{1-6}$alkyl)amino;
with the proviso that, when $R^3$ is hydrogen, then $R^4$ and $R^5$ are not both hydrogen;
and wherein any alkyl group or the alkyl moiety of any group containing such a moiety may be substituted one or more times by halo.

2. A compound according to claim 1 wherein R is $C_{1-6}$alkenyl, $C_{1-6}$alkyl, halo, or $C_{1-6}$alkoxy.

3. A compound according to claim 1 wherein R is vinyl, allyl, ethyl, methyl, fluoro, bromo, or methoxy.

4. A compound according to claim 1 wherein R is methyl, fluoro, or bromo.

5. A compound according to claim 1 wherein R is methyl.

6. A compound according to claim 1 wherein $R^1$ is hydrogen or methyl.

7. A compound according to claim 1 wherein $R^1$ is hydrogen or 4-methyl.

8. A compound according to claim 1 wherein $R^2$ is hydroxy.

9. A compound according to claim 1 wherein $R^3$ is hydrogen or methyl.

10. A compound according to claim 1 wherein $R^3$ is hydrogen.

11. A compound according to claim 1 wherein $R^4$ is hydroxy$C_{1-6}$alkyl, halo, perhalo$C_{1-6}$alkyl, $C_{1-6}$alkyl, or hydrogen.

12. A compound according to claim 1 wherein $R^4$ is hydroxymethyl, fluoro, trifluoromethyl, chloro, methyl, bromo, or hydrogen.

13. A compound according to claim 1 wherein $R^4$ is 2-hydroxymethyl, 2-F, 2-$CF_3$, 2-Cl, 2-Me, 3-Me, 2-Br, or hydrogen.

14. A compound according to claim 1 wherein $R^4$ is 2-Cl, 2-F, 2-Me, or 2-Br.

15. A compound according to claim 1 wherein $R^4$ is 2-Cl or 2-Me.

16. A compound according to claim 1 wherein $R^5$ is $C_{1-6}$alkyl, hydrogen, or halo.

17. A compound according to claim 1 wherein $R^5$ is methyl, hydrogen, fluoro, or chloro.

18. A compound according to claim 1 wherein $R^5$ is hydrogen, 6-Me, 3-F, 5-F, 6-F, or 6-Cl.

19. A compound according to claim 1 wherein $R^5$ is hydrogen, 3-F, 6-Me, 6-F, or 6-Cl.

20. A compound according to claim 1 wherein $R^5$ is 6-Me, 6-F, or 6-Cl.

21. An enantiomer of a compound of formula (I) as defined in claim 1 or a derivative thereof.

22. A mixture of enantiomers of a compound of formula (I) as defined in claim 1, or a derivative thereof, wherein one enantiomer is present in a greater proportion than its antipode.

23. A process for the preparation of a compound of formula (I) as defined in claim 1 wherein $R^2$ is hydroxy and $R^3$ is hydrogen, which process comprises the reduction of a compound of formula (II)

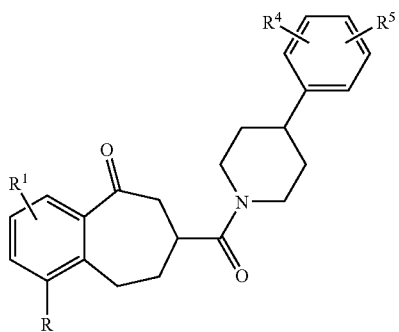

wherein;
R, $R^1$, $R^4$, and $R^5$ are as hereinbefore defined for formula (I); with a suitable reducing agent such as a metal hydride or a borane-containing reducing agent and thereafter, if required, carrying out one or more of the following optional steps:
(i) converting a compound of formula (I) to another compound of formula (I);
(ii) removing any necessary protecting group;
(iii) preparing an appropriate derivative of the compound so formed.

24. A process for the preparation of a compound of formula (I) as defined in claim 1 wherein $R^2$ is hydroxy and $R^3$ is hydrogen, which process comprises reacting a compound of formula (III)

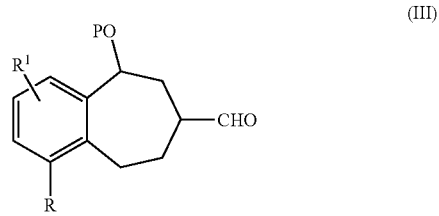

wherein;
R and $R^1$ are as hereinbefore defined for formula (I) and P represents a protecting group;
with a compound of formula (IV)

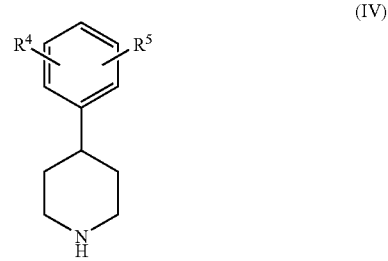

wherein;
$R^4$ and $R^5$ are as hereinbefore defined for formula (I), under reductive amination conditions followed by removal of the protecting group and thereafter, if required, carrying out one or more of the following optional steps:
(i) converting a compound of formula (I) to another compound of formula (I);
(ii) removing any necessary protecting group;
(iii) preparing an appropriate derivative of the compound so formed.

25. A process according to claim 24 wherein the protecting group, P, is a silyl group.

26. A process for the preparation of a compound of formula (I) as defined in claim 1 wherein $R^2$ is hydroxy and $R^3$ is $C_{1-6}$alkyl, which process comprises the oxidation of a compound of formula (I) as defined in claim 1 wherein $R^2$ is hydroxy and $R^3$ is hydrogen to give a compound of formula (I')

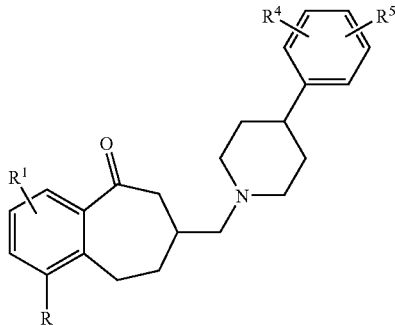

(I')

wherein;

R, $R^1$, $R^4$, and $R^5$ are as defined for formula (I) in claim 1, followed by reaction of the compound of formula (I') with a suitable organometallic compound and thereafter, if required, carrying out one or more of the following optional steps:
  (i) converting a compound of formula (I) to another compound of formula (I);
  (ii) removing any necessary protecting group;
  (iii) preparing an appropriate derivative of the compound so formed.

27. A process for the preparation of a compound of formula (I) as defined in claim 1 wherein $R^2$ is amino, $C_{1-6}$alkylamino, or di($C_{1-6}$alkyl)amino and $R^3$ is hydrogen, which process comprises the reduction of a compound of formula (VII)

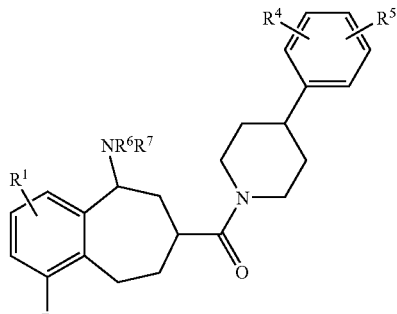

(VIII)

wherein;

R, $R^1$, $R^4$, and $R^5$ areas defined for formula (I) in claim 1 and $R^6$ and $R^7$ are each independently hydrogen or $C_{1-6}$alkyl; and thereafter, if required, carrying out one or more of the following optional steps:
  (i) converting a compound of formula (I) to another compound of formula (I);
  (ii) removing any necessary protecting group;
  (iii) preparing an appropriate derivative of the compound so formed.

28. A compound of formula (I) as defined in claim 1, or a pharmaceutically acceptable derivative thereof, as an active therapeutic substance.

29. A pharmaceutical composition comprising a compound of formula (I) as defined in claim 1, or a pharmaceutically acceptable derivative thereof, and a pharmaceutically acceptable carrier.

* * * * *